United States Patent
McGregor et al.

(10) Patent No.: US 12,275,947 B2
(45) Date of Patent: Apr. 15, 2025

(54) VIABLE GENETICALLY MODIFIED SHEEP WITH AN INACTIVATED ALPHA-1,3-GALACTOSYLTRANSFERASE (GGTA1) GENE

(71) Applicant: FIOS THERAPEUTICS, LLC, Rochester, MN (US)

(72) Inventors: Christopher G. A. McGregor, Rochester, MN (US); Irina Polejaeva, Logan, UT (US); Guerard Byrne, Minneapolis, MN (US)

(73) Assignee: FIOS THERAPEUTICS, LLC, Rochester, MN (US)

( * ) Notice: Subject to any disclaimer, the term of this patent is extended or adjusted under 35 U.S.C. 154(b) by 0 days.

(21) Appl. No.: 17/812,342

(22) Filed: Jul. 13, 2022

(65) Prior Publication Data
US 2023/0133641 A1 May 4, 2023

Related U.S. Application Data

(60) Provisional application No. 63/363,362, filed on Apr. 21, 2022, provisional application No. 63/363,229, filed on Apr. 19, 2022, provisional application No. 63/271,622, filed on Oct. 25, 2021.

(51) Int. Cl.
| | | |
|---|---|---|
| *A01K 67/027* | (2024.01) | |
| *A01K 67/0276* | (2024.01) | |
| *C12N 15/85* | (2006.01) | |

(52) U.S. Cl.
CPC ...... *C12N 15/8509* (2013.01); *A01K 67/0276* (2013.01); *A01K 2217/075* (2013.01); *A01K 2227/103* (2013.01)

(58) Field of Classification Search
None
See application file for complete search history.

(56) References Cited

U.S. PATENT DOCUMENTS

| | | |
|---|---|---|
| 7,214,344 B2 | 5/2007 | Carpentier et al. |
| 8,106,255 B2 | 1/2012 | Carroll et al. |
| 8,357,387 B2 | 1/2013 | Dove et al. |
| 2009/0311239 A1* | 12/2009 | Chtourou .......... A01K 67/0275 435/219 |
| 2011/0023159 A1 | 1/2011 | Bedell et al. |
| 2011/0281306 A1 | 11/2011 | Kim et al. |
| 2012/0192298 A1 | 7/2012 | Weinstein et al. |
| 2019/0075770 A1* | 3/2019 | Shindo .............. A01K 67/0276 |

FOREIGN PATENT DOCUMENTS

| | | |
|---|---|---|
| WO | 2017053315 A1 | 3/2017 |
| WO | 2021072777 A1 | 4/2021 |

OTHER PUBLICATIONS

Denning (Nature Biotech, 2001, vol. 19, p. 559-561) (Year: 2001).*
Zheng (Shengwu Jushu Tongxun, 2011, vol. 22, No. 4, p. 458-462, abstract only) (Year: 2011).*
Sato (Reproduction in Domestic Animals, 2015, vol. 50, No. 5, p. 872-880, abstract only) (Year: 2015).*
Choi (Transgenic Res., 2017, vol. 26, p. 209-224) (Year: 2017).*
Zhang (J. Cellular Biochem., Feb. 2019, vol. 120, p. 1794-1806) (Year: 2019).*
MGI description of GGTA1 gene (Year: 2023).*
Tearle (Transplantation, 1996, vol. 61, p. 13-19).*
Bueler (Cell, 1993, vol. 73, p. 1339-1347).*
Weissmann (Science, 1999, vol. 286, p. 914-915).*
Cas9 Alternatives Empower Next-Generation CRISPR Applications, Available Online at: https://www.twistbioscience.com/blog/science/cas9-alternatives-empower-next-generation-crispr-applications, Sep. 2, 2020, 13 pages.
Cas-Clover, Available Online at: https://www.herabiolabs.com/product/cas-clover-ccl-100/, Accessed from Internet on Sep. 1, 2022, 3 pages.
Abbasi et al., Leaflet Stress and Strain Distributions Following Incomplete Transcatheter Aortic Valve Expansion, Journal of Biomechanics, vol. 48, No. 13, Oct. 15, 2015, pp. 3663-3671.
Antonini-Canterin et al., Effect of Statins on the Progression of Bioprosthetic Aortic Valve Degeneration, The American Journal of Cardiology, vol. 92, No. 12, Dec. 15, 2003, pp. 1479-1482.
Arbustini et al., Modification by the Hancock T6 Process of Calcification of Bioprosthetic Cardiac Valves Implanted in Sheep, The American Journal of Cardiology, vol. 53, No. 9, May 1, 1984, pp. 1388-1396.
Badylak et al., Immune Response to Biologic Scaffold Materials, Seminars in Immunology, vol. 20, No. 2, Feb. 20, 2008, pp. 1-13.
Bakhtiary et al., Hydrodynamic Comparison of Biological Prostheses During Progressive Valve Calcification in a Simulated Exercise Situation. An in Vitro Study, European Journal of Cardio-thoracic Surgery, vol. 34, No. 5, Nov. 2008, pp. 960-963.

(Continued)

*Primary Examiner* — Michael C Wilson
(74) *Attorney, Agent, or Firm* — Kilpatrick Townsend & Stockton LLP

(57) ABSTRACT

Provided herein is the first viable galactosyltransferase (Gal) knock-out sheep having a deletion or mutation of alpha-1, 3-galactosyltransferase (GGTA1) gene and methods of making the same. Also provided are methods of screening a biological implant for stimulation of an antibody-mediated inflammatory response to a Gal antigen by implanting the biological implant into a recipient Gal knock-out animal and detecting signs of antibody-mediated inflammatory response in the recipient Gal knock-out animal. Further provided is a method of implanting a biological implant into a human subject by screening a first biological implant for signs of antibody-mediated inflammatory response in a recipient Gal knock-out animal and, upon detecting minimal or no signs of antibody mediated inflammatory response in the recipient Gal knock-out animal, implanting a second biological implant into the human subject, wherein the second biological implant is comparable to the first biological implant.

8 Claims, 11 Drawing Sheets

Specification includes a Sequence Listing.

(56) References Cited

OTHER PUBLICATIONS

Bell et al., Long-Term Performance of Homografts Versus Stented Bioprosthetic Valves in the Pulmonary Position in Patients Aged 10-20 Years, European Journal of Cardio-Thoracic Surgery, vol. 54, No. 5, Nov. 1, 2018, pp. 946-952.
Bibevski et al., Performance of Synergraft Decellularized Pulmonary Allografts Compared with Standard Cryopreserved Allografts: Results from Multiinstitutional Data, The Annals of Thoracic Surgery, vol. 103, No. 3, Mar. 2017, pp. 869-874.
Bloch et al., Immune Response in Patients Receiving a Bioprosthetic Heart Valve: Lack of Response with Decellularized Valves, Tissue Engineering Part A, vol. 17, Nos. 19-20, Oct. 2011, pp. 2399-2405.
Briand et al., Metabolic Syndrome Is Associated with Faster Degeneration of Bioprosthetic Valves, Circulation, vol. 114, No. 1, Jul. 4, 2006, pp. I-512-I-517.
Byrne et al., B4GALNT2 and Xenotransplantation: A newly Appreciated Xenogeneic Antigen, Xenotransplantation, vol. 25, No. 5, Sep. 2018, pp. 1-9.
Byrne et al., Recent Investigations into Pig Antigen and Anti-Pig Antibody Expression, International Journal of Surgery, vol. 23, Nov. 2015, pp. 223-228.
Capodanno et al., Standardized Definitions of Structural Deterioration and Valve Failure in Assessing Long-term Durability of Transcatheter and Surgical Aortic Bioprosthetic Valves: A Consensus Statement From the European Association of Percutaneous Cardiovascular Intervent, European Heart Journal, vol. 52, No. 3, Sep. 2017, pp. 408-417.
Carpentier et al., Biological Factors Affecting Long-term Results of Valvular Heterografts, The Journal of Thoracic and Cardiovascular Surgery, vol. 58, No. 4, Oct. 1969, pp. 467-483.
Carpentier et al., Techniques for Prevention of Calcification of Valvular Bioprostheses, Circulation, vol. 70, Sep. 1984, pp. 1165-1168.
Cebotari et al., Use of Fresh Decellularized Allografts for Pulmonary Valve Replacement May Reduce the Reoperation Rate in Children and Young Adults: Early Report, Circulation, vol. 124, Sep. 13, 2011, pp. S115-S123.
Chakravarty et al., Subclinical Leaflet Thrombosis in Surgical and Transcatheter Bioprosthetic Aortic Valves: An Observational Study, The Lancet, vol. 389, No. 10087, Mar. 19, 2017, pp. 2383-2392.
Chen et al., Mechanism of Efficacy of 2-Amino Oleic Acid for Inhibition of Calcification of Glutaraldehyde-Pretreated Porcine Bioprosthetic Heart Valves, Circulation, vol. 90, No. 1, Jul. 1994, pp. 323-329.
Chylinski et al., The TracrRNA and Cas9 Families of Type II CRISPR-Cas Immunity Systems, RNA Biology, vol. 10, No. 5, May 2013, pp. 726-737.
Colvin et al., Aging and the Immune Response to Organ Transplantation, Journal of Clinical Investigation, vol. 127, No. 7, Jul. 2017, pp. 2523-2529.
Commins et al., Delayed Anaphylaxis, Angioedema, or Urticaria After Consumption of Red Meat in Patients with IgE Antibodies Specific for Galactose-α-1,3-Galactose, The Journal of Allergy and Clinical Immunology, vol. 123, No. 2, Feb. 2009, pp. 426-433.
Connolly, Triglycidyl Amine Crosslinking Combined with Ethanol Inhibits Bioprosthetic Heart Valve Calcification, The Annals of Thoracic Surgery, vol. 92, No. 3, Sep. 1, 2011, pp. 858-865.
Costa et al., Long-term Transcatheter Aortic Valve Durability, Journal of Interventional Cardiology, vol. 14, No. 2, May 21, 2019, pp. 62-69.
Cote et al., Incidence, Risk Factors, Clinical Impact, and Management of Bioprosthesis Structural Valve Degeneration, Current Opinion in Cardiology, vol. 32, No. 2, Mar. 2017, pp. 123-129.
Culler et al., Trends in Aortic Valve Replacement Procedures Between 2009 and 2015: Has Transcatheter Aortic Valve Replacement Made a Difference? The Annals of Thoracic Surgery, vol. 105, No. 4, Apr. 2018, pp. 1137-1143.

Cunanan et al., Tissue Characterization and Calcification Potential of Commercial Bioprosthetic Heart Valves, The Annals of Thoracic Surgery, vol. 71, No. 5, May 2001, pp. S417-S421.
David et al., Aortic Valve Replacement with Toronto SPV Bioprosthesis: Optimal Patient Survival but Suboptimal Valve Durability, Journal of Thoracic and Cardiovascular Surgery, vol. 135, No. 1, Jan. 2008, pp. 19-24.
David et al., Hancock II Bioprosthesis for Aortic Valve Replacement: the Gold Standard of Bioprosthetic Valves Durability? The Annals of Thoracic Surgery, vol. 90, No. 3, Sep. 2010, pp. 775-781.
Denning et al., Gene Targeting in Primary Fetal Fibroblasts from Sheep and Pig, Cloning and Stem Cells, vol. 3, No. 4, 2001, pp. 221-231.
Denning et al., Deletion of the α(1,3) galactosyl transferase (GGTA1) gene and the prion protein (PrP) gene in sheep, Nature Biotechnology, vol. 19, Jun. 2001, pp. 559-562.
Duarte et al., In Vivo Hemodynamic, Histologic, and Antimineralization Characteristics of the Mosaic Bioprosthesis, The Annals of Thoracic Surgery, vol. 71, No. 1, Jan. 2001, pp. 92-99.
Durand et al., Preoperative Statin Treatment Is Not Associated with Reduced Postoperative Mortality or Morbidity in Patients Undergoing Isolated Valve Surgery, The Heart Surgery Forum, vol. 22, No. 1, Feb. 21, 2019, pp. E057-E062.
Dvir et al., Standardized Definition of Structural Valve Degeneration for Surgical and Transcatheter Bioprosthetic Aortic Valves, Circulation, vol. 137, No. 4, Jan. 23, 2018, pp. 388-399.
Fan et al., A Sheep Model of Cystic Fibrosis Generated By CRISPR/Cas9 Disruption of the CFTR Gene, JCI Insight, vol. 3, No. 19, Oct. 2018, pp. 1-12.
Fang et al., Anti-Gal Antibodies in α1, 3-Galactosyltransferase Gene-Knockout Pigs, Xenotransplantation, vol. 19, No. 5, Sep. 2012, pp. 305-310.
Farivar et al., Hypercholesterolemia is a Risk Factor for Bioprosthetic Valve Calcification and Explantation, The Journal of Thoracic and Cardiovascular Surgery, vol. 126, No. 4, Apr. 21, 2003, pp. 969-975.
Flameng et al., A Randomized Assessment of an Advanced Tissue Preservation Technology in the Juvenile Sheep Model, The Journal of Thoracic and Cardiovascular Surgery, vol. 149, No. 1, Jan. 2015, pp. 340-345.
Fournier et al., A Deadly Aversion to Pork, Lancet, vol. 377, No. 9776, Apr. 30, 2011, p. 1542.
Galili et al., Man, Apes, and Old World Monkeys Differ from Other Mammals in the Expression of Alpha-Galactosyl Epitopes on Nucleated Cells, The Journal of Biological Chemistry, vol. 263, No. 33, Nov. 25, 1988, pp. 17755-17762.
Galili et al., One Percent of Human Circulating B Lymphocytes Are Capable of Producing the Natural Anti-Gal Antibody, Blood, vol. 82, No. 8, Oct. 1993, pp. 2485-2493.
Goldstein et al., Transpecies Heart Valve Transplant: Advanced Studies of a Bioengineered Xeno-Autograft, The Annals of Thoracic Surgery, vol. 70, No. 6, 2000, pp. 1962-1969.
Goldstone et al., Mechanical or Biologic Prostheses for Aortic-Valve and Mitral-Valve Replacement, The New England Journal of Medicine, vol. 377, No. 19, Nov. 9, 2017, pp. 1847-1857.
Gott et al., Refinement of the Alpha Aminooleic Acid Bioprosthetic Valve Anticalcification Technique, The Annals of Thoracic Surgery, vol. 64, No. 1, Jul. 1997, pp. 50-58.
Grimm et al., Improved Biocompatibility of Bioprosthetic Heart Valves by L-glutamic Acid Treatment, Journal of Cardiac Surgery, vol. 7, No. 1, Mar. 1992, pp. 58-64.
Guo et al., Molecular Cloning of the B4GALNT2 Gene and Its Single Nucleotide Polymorphisms Association with Litter Size in Small Tail Han Sheep, Animals, vol. 8, No. 10, Sep. 2008, pp. 1-14.
Gura et al., Identification of Specific Calcium-Binding Noncollagenous Proteins Associated with Glutaraldehyde-Preserved Bovine Pericardium in the Rat Subdermal Model, Journal of Biomedical Materials Research, vol. 35, No. 4, Jun. 15, 1997, pp. 483-495.
Hawkins et al., Premature Bioprosthetic Aortic Valve Degeneration Associated with Allergy to Galactose-Alpha-1,3-Galactose, Journal of Cardiac Surgery, vol. 31, No. 7, Jul. 2016, pp. 446-448.
Hou et al., Efficient Genome Engineering in Human Pluripotent Stem Cells Using Cas9 From Neisseria Meningitidis, Proceedings

(56) References Cited

OTHER PUBLICATIONS of the National Academy of Sciences of the United States of America, vol. 110, No. 39, Sep. 24, 2013, pp. 15644-15649.
Huded et al., Relation of Intensity of Statin Therapy and Outcomes After Transcatheter Aortic Valve Replacement, The American Journal of Cardiology, vol. 119, No. 11, Jun. 1, 2017, pp. 1832-1838.
Human et al., Characterization of the Immune Response to Valve Bioprostheses and Its Role in Primary Tissue Failure, The Annals of Thoracic Surgery, vol. 71, May 2001, pp. S385-S388.
Human et al., Inflammatory and Immune Processes: The Neglected Villain of Bioprosthetic Degeneration? Journal of Long-Term Effects of Medical Implants, vol. 11, Nos. 3-4, 2001, pp. 199-220.
Isaacs et al., National Trends in Utilization and in-hospital Outcomes of Mechanical Versus Bioprosthetic Aortic Valve Replacements, The Journal of Thoracic and Cardiovascular Surgery, Acquired Cardiovascular Disease: Aortic Valve vol. 149, No. 5, May 2015, pp. 1262-1269.
Jamieson et al., Carpentier-Edwards Standard Porcine Bioprosthesis: Primary Tissue Failure (Structural Valve Deterioration) by Age Groups, The Annals of Thoracic Surgery, vol. 46, No. 2, Aug. 1988, pp. 155-162.
Jinek et al., A Programmable Dual-RNA-Guided DNA Endonuclease in Adaptive Bacterial Immunity, Science, vol. 337, No. 6096, Aug. 17, 2012, pp. 816-821.
Johnston et al., Long-Term Durability of Bioprosthetic Aortic Valves: Implications From 12,569 Implants, The Annals of Thoracic Surgery, vol. 99, No. 4, Apr. 2015, pp. 1239-1247.
Kasimir et al., Presence and Elimination of the Xenoantigen Gal ($\alpha$1, 3) Gal in Tissue-Engineered Heart Valves, Tissue Engineering, vol. 11, Nos. 7-8, Jul.-Aug. 2005, pp. 1274-1280.
Khan et al., Pathological Findings in Explanted Prosthetic Heart Valves from Ventricular Assist Devices, Pathology, vol. 40, No. 4, Jun. 2008, pp. 377-384.
Kiefer et al., Crimping May Affect the Durability of Transcatheter Valves: An Experimental Analysis, Original Article Adult Cardiac, vol. 92, No. 1, Available Online at: http://dx.doi.org/10.1016/j.athoracsur.2011.03.020, Mar. 9, 2011, pp. 155-160.
Kim et al., Differences in Xenoreactive Immune Response and Patterns of Calcification of Porcine and Bovine Tissues in $\alpha$-Gal Knock-Out and Wild-Type Mouse Implantation Models, European Journal of Cardio-Thoracic Surgery, vol. 48, No. 3, Sep. 2015, pp. 392-399.
Konakci et al., Alpha-Gal on Bioprostheses: Xenograft Immune Response in Cardiac Surgery, European Journal of Clinical Investigation, vol. 35, No. 1, Jan. 2005, pp. 17-23.
Kostyunin et al., Degeneration of Bioprosthetic Heart Valves: Update 2020, Journal of the American Heart Association, vol. 9, No. 19, Sep. 2020, pp. 1-19.
Kulik et al., Postoperative Lipid-lowering Therapy and Bioprosthesis Structural Valve Deterioration: Justification for a Randomised Trial? European Journal of Cardio-Thoracic Surgery, vol. 37, No. 1, Jan. 2010, pp. 139-144.
Kuravi et al., Allergic Response to Medical Products in Patients with Alpha-Gal Syndrome, The Journal of Thoracic and Cardiovascular Surgery, vol. 164, No. 6, Dec. 2021, pp. e411-e424.
Lee et al., High-Concentration Glutaraldehyde Fixation of Bovine Pericardium in Organic Solvent and Post-Fixation Glycine Treatment: In Vitro Material Assessment and in Vivo Anticalcification Effect, European Journal of Cardio-Thoracic Surgery, vol. 39, No. 3, Mar. 2011, pp. 381-387.
Lee et al., Human Antibody Recognition of Xenogeneic Antigens (NeuGc and Gal) on Porcine Heart Valves: Could Genetically Modified Pig Heart Valves Reduce Structural Valve Deterioration? Xenotransplantation, vol. 23, No. 5, Sep. 2016, pp. 370-380.
Lee et al., Immune Response to Bovine Pericardium Implanted into $\alpha$1,3-Galactosyltransferase Knockout Mice: Feasibility as an Animal Model for Testing Efficacy of Anticalcification Treatments of Xenografts, European Journal of Cardio-Thoracic Surgery, vol. 42, No. 1, Jul. 2012, pp. 164-172.

Levy et al., Vitamin K-dependent Calcium Binding Proteins in Aortic Valve Calcification, The Journal of Clinical Investigation, vol. 65, No. 2, Feb. 1980, pp. 563-566.
Li et al., Cas-CLOVER™: A High-Fidelity Genome Editing System for Safe and Efficient Modification of Cells for Immunotherapy, Precision CRISPR Congress Poster Presentation, 2018, 1 page.
Li et al., Generation of Biallelic Knock-out Sheep Via Gene-editing And Somatic Cell Nuclear Transfer, Scientific Reports, vol. 6, No. 1, Sep. 2016, pp. 1-12.
Liao et al., Mechanical Stress: An Independent Determinant of Early Bioprosthetic Calcification in Humans, The Annals of Thoracic Surgery, vol. 86, No. 2, Aug. 2008, pp. 491-495.
Lila et al., Gal Knockout Pig Pericardium: New Source of Material for Heart Valve Bioprostheses, The Journal of Heart and Lung Transplantation, vol. 29, No. 5, May 2010, pp. 538-543.
Lim et al., In Vivo Efficacy of Alpha-Galactosidase as Possible Promise for Prolonged Durability of Bioprosthetic Heart Valve Using Alpha1,3-Galactosyltransferase Knockout Mouse, Tissue Engineering Part A, vol. 19, Nos. 21-22, Nov. 2013, pp. 2339-2348.
Lu et al., Xenotransplantation: Current Status in Preclinical Research, Frontiers in Immunology, vol. 10, No. 3060, Jan. 23, 2020, pp. 1-19.
Makarova et al., Evolution and Classification of the CRISPR-Cas Systems, Nature Reviews Microbiology, vol. 9, No. 6, Jun. 2011, pp. 467-477.
Makkar et al., Possible Subclinical Leaflet Thrombosis in Bioprosthetic Aortic Valves, The New England Journal of Medicine, vol. 373, No. 21, Nov. 19, 2015, pp. 2015-2024.
Mangold et al., Alpha-Gal Specific IgG Immune Response After Implantation of Bioprostheses, The Thoracic and Cardiovascular Surgeon, vol. 57, No. 4, Jun. 2009, pp. 191-195.
Masters et al., Long-Term Experience with the lonescu-Shiley Pericardial Valve, The Annals of Thoracic Surgery, vol. 60, Aug. 1995, pp. S288-S291.
Mathapati et al., Inflammatory Responses of Tissue-Engineered Xenografts in a Clinical Scenario, Interactive CardioVascular and Thoracic Surgery, vol. 12, No. 3, Mar. 2011, pp. 360-365.
Mcgregor et al., Biological Equivalence of GGTA-1 Glycosyltransferase Knockout and Standard Porcine Pericardial Tissue Using 90-Day Mitral Valve Implantation in Adolescent Sheep, Cardiovascular Engineering and Technology, vol. 13, No. 3, Jun. 2022, pp. 363-372.
Mcgregor et al., Cardiac Xenotransplantation Technology Provides Materials for Improved Bioprosthetic Heart Valves, The Journal of Thoracic and Cardiovascular Surgery, vol. 141, No. 1, Jan. 2011, pp. 269-275.
Mcgregor et al., Gal-Knockout Bioprostheses Exhibit Less Immune Stimulation Compared to Standard Biological Heart Valves, Journal of Heart Valve Disease, vol. 22, No. 3, May 2013, pp. 383-390.
Mcgregor et al., Physical Equivalency of Wild Type and Galactose $\alpha$ 1,3 Galactose Free Porcine Pericardium; A New Source Material for Bioprosthetic Heart Valves, Acta Biomaterialia, vol. 41, Sep. 1, 2016, pp. 204-209.
Meuris et al., A Novel Tissue Treatment to Reduce Mineralization of Bovine Pericardial Heart Valves, The Journal of Thoracic and Cardiovascular Surgery, vol. 156, No. 1, Jul. 2018, pp. 197-206.
Meyer et al., Does Metabolic Syndrome Influence Bioprosthetic Mitral Valve Degeneration and Reoperation Rate? Journal of Cardiac Surgery, vol. 27, No. 2, Mar. 2012, pp. 146-151.
Midha et al., The Fluid Mechanics of Transcatheter Heart Valve Leaflet Thrombosis in the Neo-Sinus, Circulation, vol. 136, No. 17, Oct. 24, 2017, pp. 1598-1609.
Moczar et al., Complement Activation is Involved in the Structural Deterioration of Bovine Pericardial Bioprosthetic Heart Valves, ASAIO Journal, vol. 42, No. 5, Sep.-Oct. 1996, pp. M375-M381.
Moczar et al., Structural Changes in Porcine Bioprosthetic Valves of a Left Ventricular Assist System in Human Patients, Journal of Heart Valve Disease, vol. 9, No. 1, Jan. 2000, pp. 88-96.
Mozzicato et al., Porcine or Bovine Valve Replacement in Three Patients with IgE Antibodies to the Mammalian Oligosaccharide Galactose-Alpha-1,3-Galactose, The Journal of Allergy and Clinical Immunology, vol. 2, No. 5, Sep.-Oct. 2014, pp. 637-638.
Mylotte et al., Transcatheter Heart Valve Failure: A Systematic Review, European Heart Journal, vol. 36, No. 21, Jun. 1, 2015, 25 pages.

(56) References Cited

OTHER PUBLICATIONS

Nair et al., Characterizing the Inflammatory Reaction in Explanted Medtronic Freestyle Stentless Porcine Aortic Bioprosthesis Over a 6-Year Period, Cardiovascular Pathology: The Official Journal of the Society for Cardiovascular Pathology, vol. 21, No. 3, May-Jun. 2012, pp. 158-168.
Naso et al., Alpha-Gal Inactivated Heart Valve Bioprostheses Exhibit an Anti-Calcification Propensity Similar to Knockout Tissues, Tissue Engineering Part A, vol. 23, Nos. 19-20, Oct. 2017, pp. 1181-1195.
Naso et al., First Quantification of Alpha-Gal Epitope in Current Glutaraldehyde-Fixed Heart Valve Bioprostheses, Xenotransplantation, vol. 20, No. 4, Jul.-Aug. 2013, pp. 252-261.
Nishimura et al., 2017 AHA/ACC Focused Update of the 2014 AHA/ACC Guideline for the Management of Patients With Valvular Heart Disease: A Report of the American College of Cardiology/ American Heart Association Task Force on Clinical Practice Guidelines, Circulation, vol. 135, No. 25, Jun. 20-27, 2017, pp. e1159-e1195.
Nollert et al., Risk Factors for Atherosclerosis and the Degeneration of Pericardial Valves After Aortic Valve Replacement, The Journal of Thoracic and Cardiovascular Surgery, Surgery for Acquired Cardiovascular Disease, vol. 126, No. 4, Oct. 28, 2002, pp. 965-968.
O'Brien et al., The SynerGraft Valve: A New Acellular (Nonglutaraldehyde-Fixed) Tissue Heart Valve for Autologous Recellularization First Experimental Studies Before Clinical Implantation, Seminars in Thoracic and Cardiovascular Surgery, vol. 11, Oct. 1999, pp. 194-200.
Otto et al., 2020 ACC/AHA Guideline for the Management of Patients with Valvular Heart Disease: Executive Summary: A Report of the American College of Cardiology/American Heart Association Joint Committee on Clinical Practice Guidelines, Circulation, vol. 143, No. 5, Feb. 2, 2021, pp. e35-e71.
Park et al., Anti α-Gal Immune Response Following Porcine Bioprosthesis Implantation in Children, Journal of Heart Valve Disease, vol. 19, No. 1, Jan. 2010, pp. 124-130.
International Application No. PCT/US2022/078652, International Search Report and Written Opinion mailed on Jan. 24, 2023, 15 pages.
Peri-Okonny et al., Association of Statin Use and Mortality After Transcatheter Aortic Valve Replacement, Journal of the American Heart Association, vol. 8, No. 8, 2019, 18 pages.
Perisse et al., Improvements in Gene Editing Technology Boost its Applications in Livestock, Frontiers in Genetics, vol. 11, No. 614688, Jan. 8, 2021, pp. 1-21.
Platt et al., Acute Vascular Rejection, Xenotransplantation, vol. 5, 1998, pp. 169-175.
Polejaeva, 25th Anniversary of Cloning by Somatic Cell Nuclear Transfer: Generation of Genetically Engineered Livestock Using Somatic Cell Nuclear Transfer, Reproduction, vol. 162, No. 1, Jun. 16, 2021, pp. F11-F22.
Raeder et al., Natural Anti-galactose Alpha1,3 Galactose Antibodies Delay, But Do Not Prevent the Acceptance of Extracellular Matrix Xenografts, Transplant Immunology, vol. 10, No. 1, Jun. 2002, pp. 15-24.
Rahmani et al., A Durable Porcine Pericardial Surgical Bioprosthetic Heart Valve: A Proof of Concept, Journal of Cardiovascular Translational Research, vol. 12, No. 4, Aug. 2019, pp. 331-337.
Salmonsmith et al., Does Transcatheter Aortic Valve Alignment Matter? Open Heart, vol. 6, No. 2, Nov. 21, 2019, 10 pages.
Sampson et al., A Crispr/Cas System Mediates Bacterial Innate Immune Evasion and Virulence, Nature, vol. 497, No. 7448, May 9, 2013, pp. 254-257.
Schoen et al., Tissue Heart Valves: Current Challenges and Future Research Perspectives, Journal of Biomedical Materials Research, Founder's Award, 25th Annual Meeting of the Society for Biomaterials, Providence, vol. 47, Apr. 28-May 2, 1999, pp. 439-465.
Scully et al., Five-Year Follow-Up of Hancock Pericardial Valves: Management of Premature Failure, Journal of Cardiac Surgery, vol. 3, Sep. 1988, pp. 397-403.
Sellers et al., Transcatheter Aortic Heart Valves: Histological Analysis Providing Insight to Leaflet Thickening and Structural Valve Degeneration, JACC: Cardiovascular Imaging, vol. 12, No. 1, Jan. 2019, pp. 135-145.
Senage et al., The Role of Antibody Responses Against Glycans in Bioprosthetic Heart Valve Calcification and Deterioration, Nature Medicine, vol. 28, No. 2, 2022, 26 pages.
Shen et al., Osteopontin is Associated With Bioprosthetic Heart Valve Calcification in Humans, Comptes Rendus de l'Academie des Sciences—Series III—Sciences de la Vie, vol. 320, No. 1, Jan. 1997, pp. 49-57.
Simionescu, Prevention of Calcification in Bioprosthetic Heart Valves: Challenges and Perspectives, Expert Opinion on Biological Therapy, vol. 4, No. 12, Dec. 2004, pp. 1971-1985.
Simon et al., Early Failure of the Tissue Engineered Porcine Heart Valve Synergraft™ in Pediatric Patients, European Journal of Cardio-Thoracic Surgery, vol. 23, No. 6, Jun. 2003, pp. 1002-1006.
Skowasch et al., Cells of Primarily Extravalvular Origin in Degenerative Aortic Valves and Bioprostheses, European Heart Journal, vol. 26, No. 23, Dec. 2005, pp. 2576-2580.
Skowasch et al., Tissue Resident C Reactive Protein in Degenerative Aortic Valves: Correlation with Serum C Reactive Protein Concentrations and Modification by Statins, Heart, vol. 92, No. 4, Apr. 2006, pp. 495-498.
Slaymaker et al., Rationally Engineered Cas9 Nucleases with Improved Specificity, Science, vol. 351, No. 6268, Jan. 1, 2016, pp. 84-88.
Spray et al., Structural Changes in Porcine Xenografts Used as Substitute Cardiac Valves. Gross and Histologic Observations in 51 Glutaraldehyde-Preserved Hancock Valves in 41 Patients, American Journal of Cardiology, vol. 40, No. 3, Sep. 1, 1977, pp. 319-330.
Srivatsa et al., Increased Cellular Expression of Matrix Proteins that Regulate Mineralization is Associated with Calcification of Native Human and Porcine Xenograft Bioprosthetic Heart Valves, The Journal of Clinical Investigation, vol. 99, No. 5, Mar. 1, 1997, pp. 996-1009.
Stone et al., Anterior Cruciate Ligament Reconstruction with a Porcine Xenograft: A Serologic, Histologic, and Biomechanical Study in Primates, Arthroscopy, vol. 23, No. 4, Apr. 2007, pp. 411-419.
Stone et al., Replacement of Human Anterior Cruciate Ligaments with Pig Ligaments: A Model for Anti-Non-Gal Antibody Response in Long-Term Xenotransplantation, Transplantation, vol. 83, No. 2, Jan. 27, 2007, pp. 211-219.
Takagi et al., Meta-Analysis for Impact of Statin on Mortality After Transcatheter Aortic Valve Implantation, The American Journal of Cardiology, vol. 124, No. 6, Sep. 15, 2019, pp. 920-925.
Tod et al., The Association of Bound Aldehyde Content with Bioprosthetic Tissue Calcification, Journal of Materials Science: Materials in Medicine, vol. 27, No. 1, Jan. 2016, 7 pages.
Valente et al., Ultrastructural Substrates of Dystrophic Calcification in Porcine Bioprosthetic Valve Failure, The American Journal of Pathology, vol. 119, No. 1, Apr. 1985, pp. 12-21.
Van Wachem et al., In Vivo Behavior of Epoxy-Crosslinked Porcine Heart Valve Cusps and Walls, Journal of Biomedical Materials Research, vol. 53, No. 1, 2000, pp. 18-27.
Vongpatanasin et al., Prosthetic Heart Valves, The New England Journal of Medicine, vol. 335, No. 6, Aug. 8, 1996, pp. 407-416.
Vyavahare et al., Prevention of Bioprosthetic Heart Valve Calcification by Ethanol Preincubation: Efficacy and Mechanisms, Circulation, vol. 95, No. 2, Jan. 21, 1997, pp. 479-488.
Wang et al., Antigenicity of Tissues and Organs from GGTA1/ CMAH/β4GaINT2 Triple Gene Knockout Pigs, The Journal of Biomedical Research, vol. 33, No. 4, Jul. 2018, pp. 235-243.
Wang et al., Bioprosthetic Aortic Valve Durability: A Meta-regression of Published Studies, The Annals of Thoracic Surgery, vol. 104, No. 3, Sep. 2017, pp. 1080-1087.
Wang et al., Eliminating Xenoantigen Expression on Swine RBC, Transplantation, vol. 101, No. 3, Mar. 2017, pp. 517-523.
Wang et al., Variations in Activity of the Human Natural Anti-Gal Antibody in Young and Elderly Populations, The Journals of Gerontology. Series A, Biological Sciences and Medical Sciences, vol. 50, No. 4, Jul. 1995, pp. M227-M233.

(56) References Cited

OTHER PUBLICATIONS

Weber et al., Evidence of Mitigated Calcification of the Mosaic Versus Hancock Standard Valve Xenograft in the Mitral Position of Young Sheep, The Journal of Thoracic and Cardiovascular Surgery, vol. 132, No. 5, Nov. 2006, pp. 1137-1143.
Wei et al., α-Gal Antigen-Deficient Rabbits with GGTA1 Gene Disruption Via CRISPR/Cas9, BMC Genomic Data, vol. 23, No. 1, Jul. 2022, pp. 1-10.
Xu et al., The Structure of Anti-Gal Immunoglobulin Genes in Naive and Stimulated Gal Knockout Mice, Transplantation, vol. 72, No. 11, Dec. 2001, pp. 1817-1825.
Yang et al., Oocytes from Small and Large Follicles Exhibit Similar Development Competence Following Goat Cloning Despite Their Differences in Meiotic and Cytoplasmic Maturation, Theriogenology, vol. 86, No. 9, Dec. 2016, 25 pages.
Yoganathan et al., Fluid Mechanics of Heart Valves, Annual Review of Biomedical Engineering, vol. 6, 2004, pp. 331-362.
Zetsche et al., Cpf1 is a Single RNA-Guided Endonuclease of a Class 2 CRISPR-Cas System, Cell, vol. 163, No. 3, Oct. 22, 2015, pp. 759-771.
Zhang et al., Preclinical Assessment of Cardiac Valve Substitutes: Current Status and Considerations for Engineered Tissue Heart Valves, Frontiers in Cardiovascular Medicine, vol. 6, No. 72, Jun. 7, 2019, pp. 1-9.
Zhang et al., Reducing Immunoreactivity of Porcine Bioprosthetic Heart Valves by Genetically-Deleting Three Major Glycan Antigens GGTA1/B4GalNT2/CMAH, Acta Biomaterialia, vol. 72, May 2018, pp. 196-205.
International Application No. PCT/US2022/078652, "International Preliminary Report on Patentability", May 10, 2024, 9 pages.

\* cited by examiner

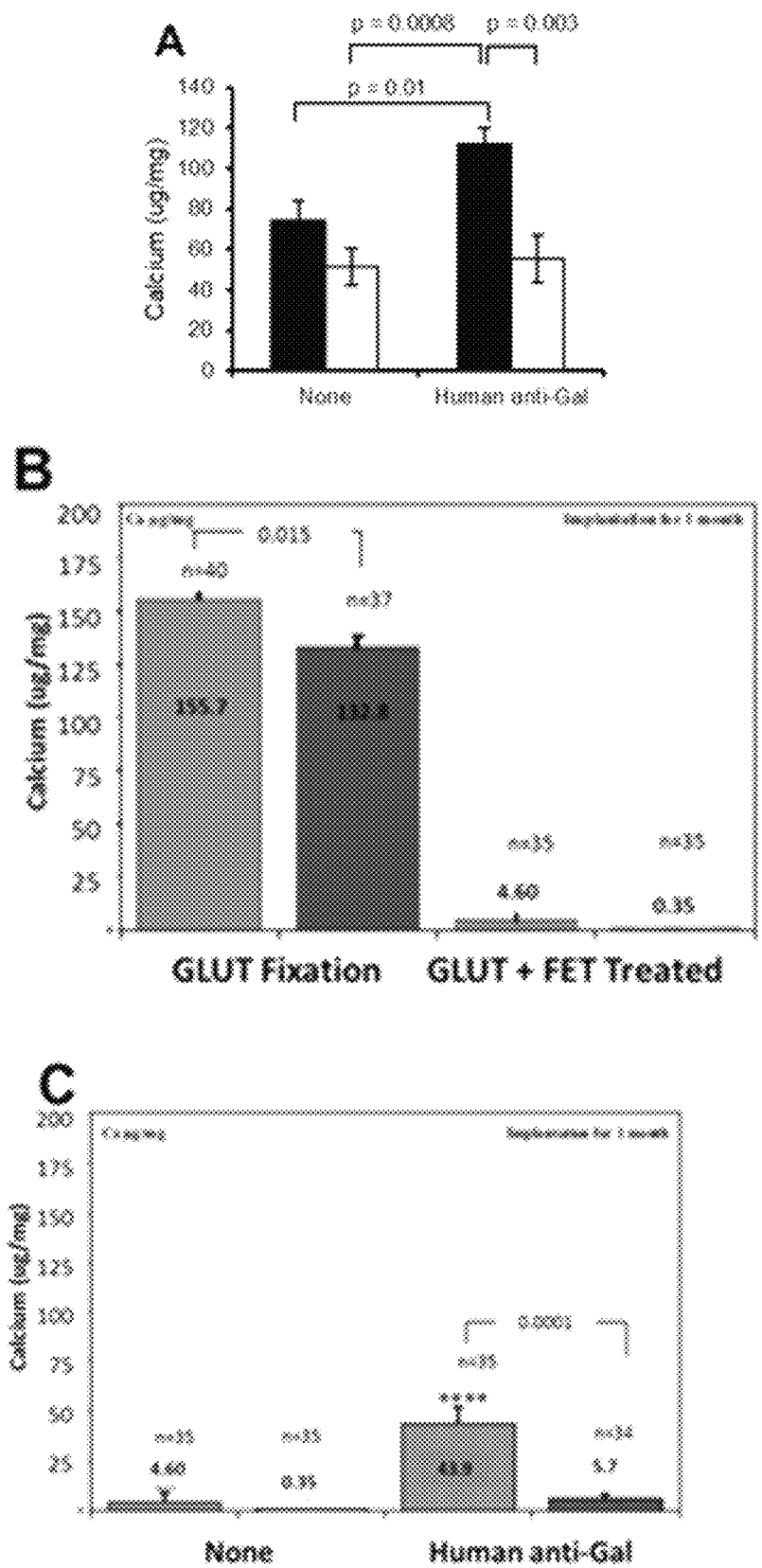
FIGS. 2A-C

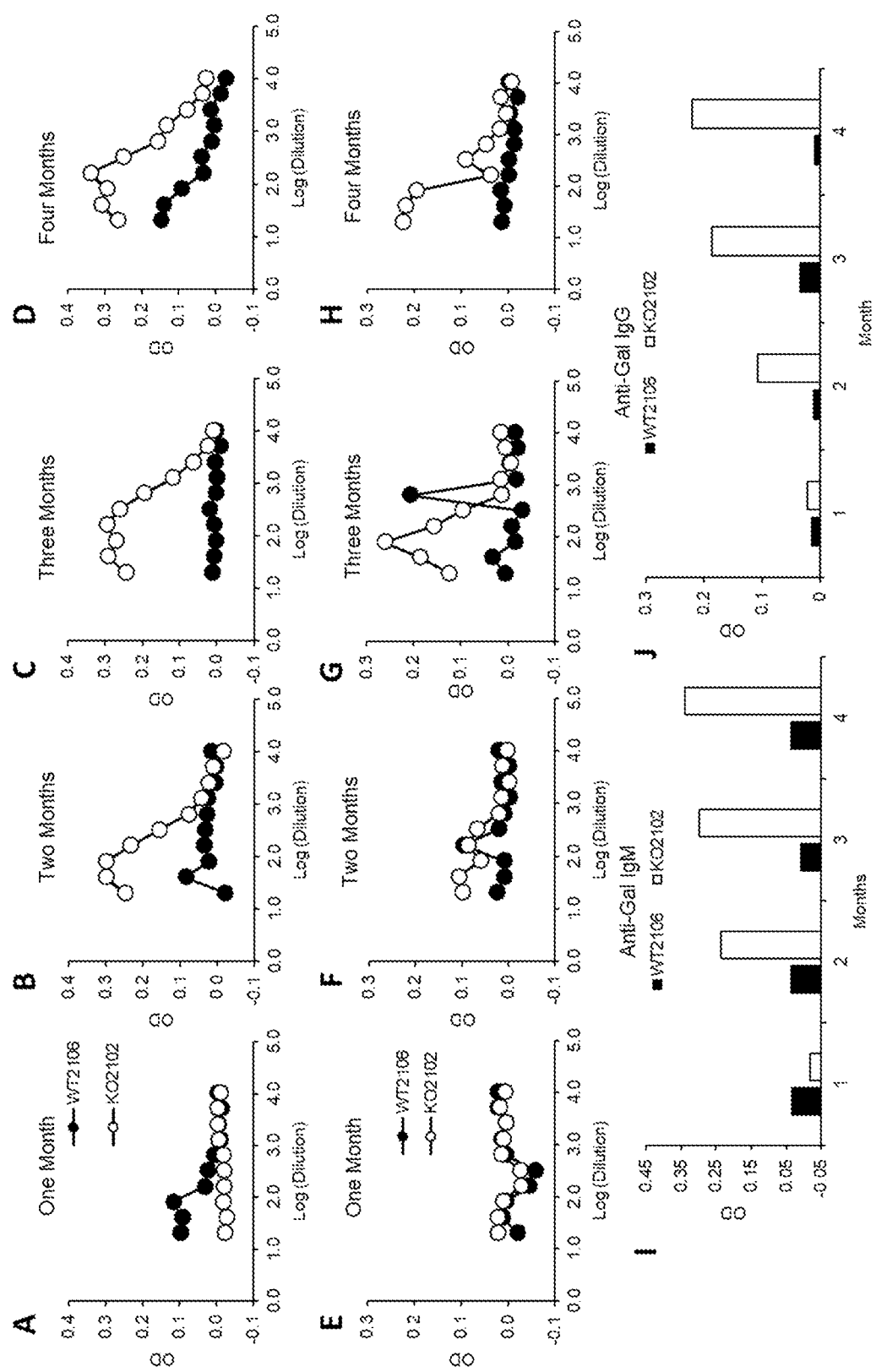
FIGS. 5A-J

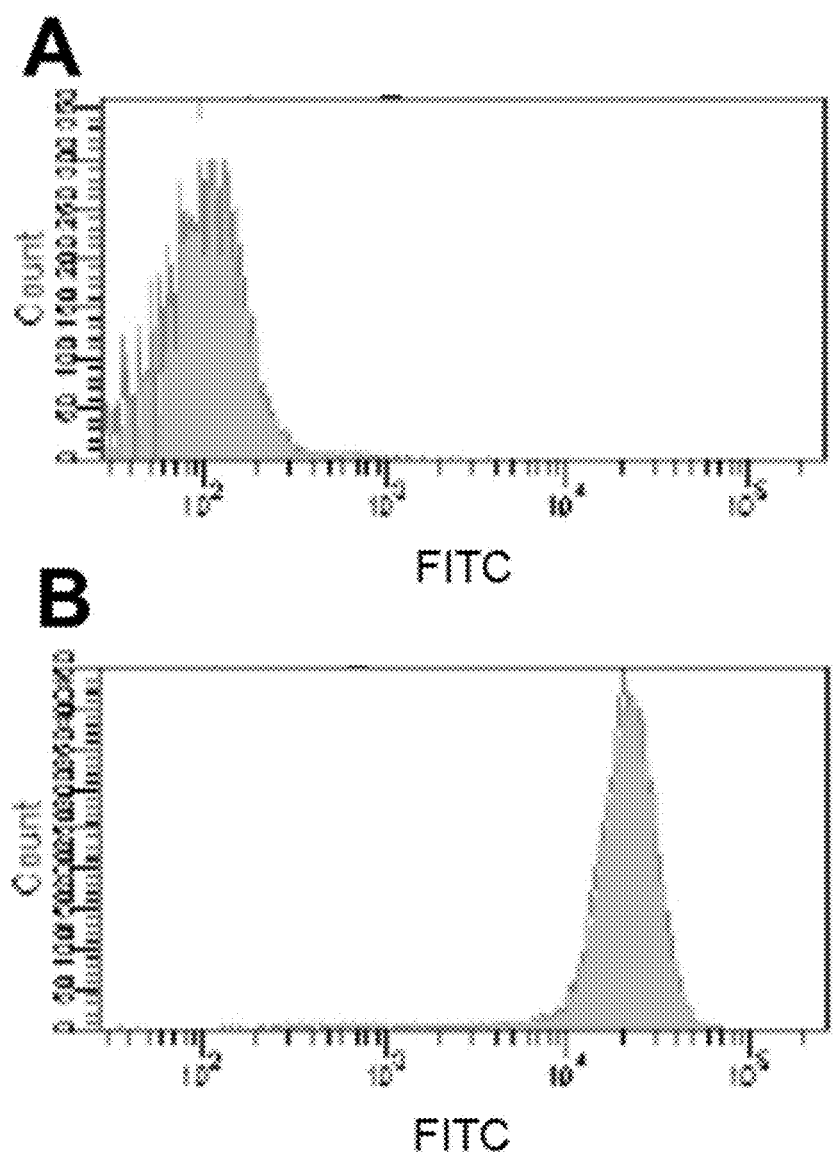
FIGS. 6A-B

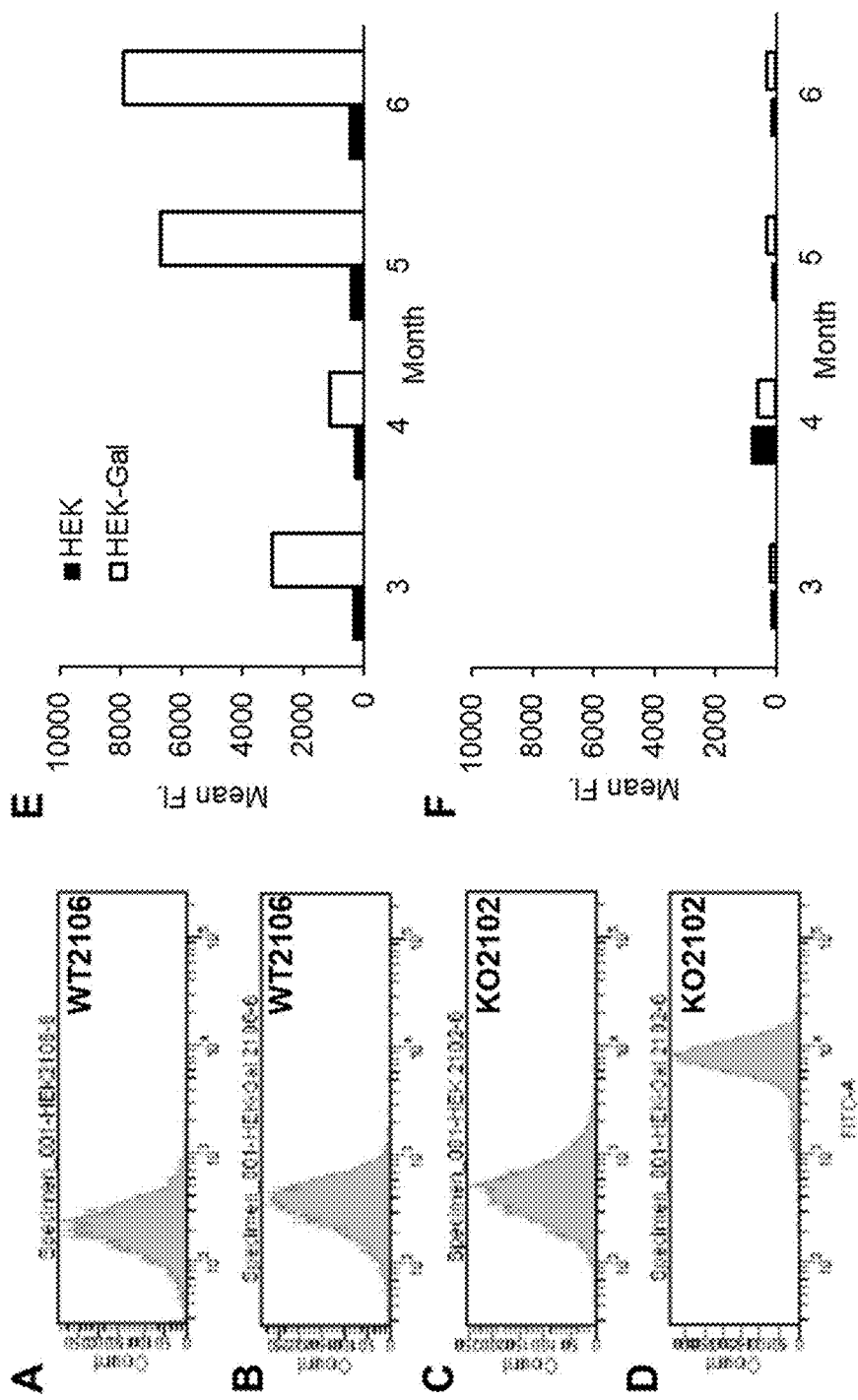
FIGS. 7A-F

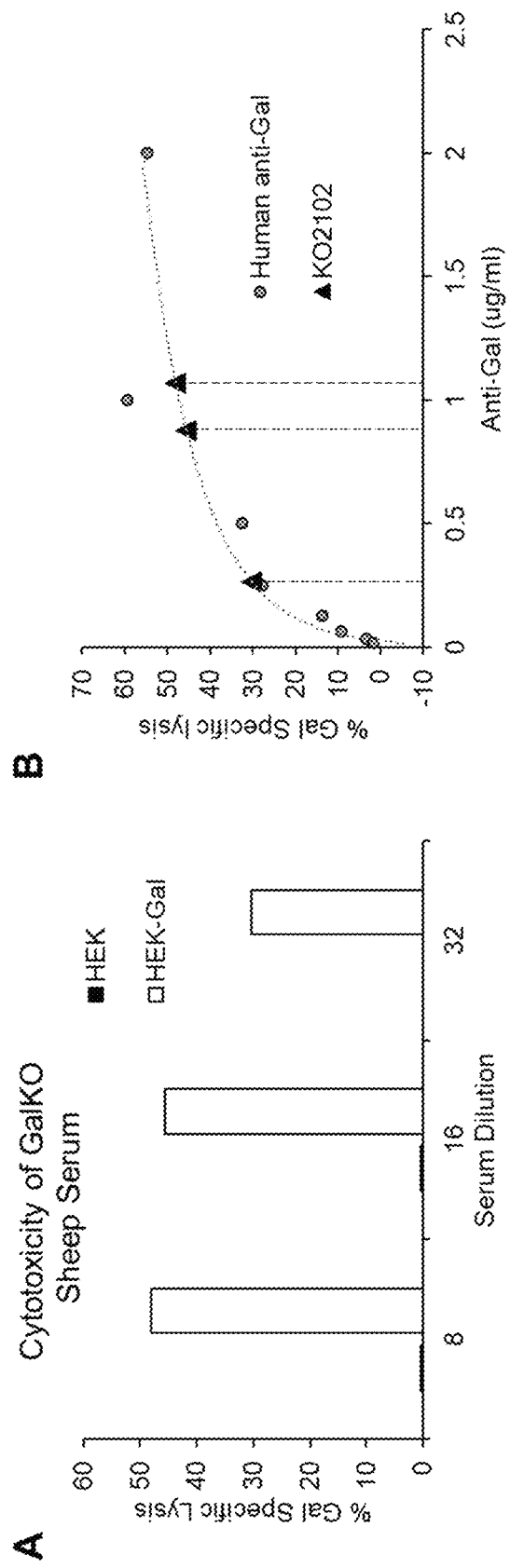
FIGS. 8A-B

VIABLE GENETICALLY MODIFIED SHEEP WITH AN INACTIVATED ALPHA-1,3-GALACTOSYLTRANSFERASE (GGTA1) GENE

CROSS-REFERENCE TO RELATED APPLICATIONS

This application claims the benefit of U.S. Provisional Application No. 63/271,622, filed Oct. 25, 2021, U.S. Provisional Application No. 63/363,229 filed Apr. 19, 2022, and U.S. Provisional Application No. 63/363,362, filed Apr. 21, 2022. The above-listed applications are hereby incorporated herein by this reference in their entireties.

BACKGROUND

Animal tissues are widely used as non-viable clinical replacement tissues, surgical meshes and other forms of implants, for example, heart valves, skin, bone, or engineered tissues. Viable animal tissues and organs are actively being investigated as a clinical source for transplantation. However, implantation of any foreign biological organ, tissue, or cell, viable or not, poses significant obstacles, including rejection, where the body recognizes the implant as foreign and mounts an immune response against it. Although the risk of implant rejection can be reduced by the use of immunosuppressive drugs, these drugs have multiple negative side effects, including higher rates of cancer and infections which preclude their use in all but the most essential life-saving procedures, such as organ transplantation. Screening an organ, tissue, or cells for antigens that provoke an immune response is dependent on the animal model and may be insufficient when an antigen within an implant is not recognized by the immune system of the animal model. This occurred during the development of an acellular porcine heart valve, where its performance in standard sheep models was excellent but residual xenogeneic antigenicity in the form of the galactose alpha 1,3 galactose carbohydrate (Gal) resulted in catastrophic clinical valve failure and multiple deaths (O'Brien et al., *Semin. Thorac. Cardiovasc. Surg.* 11, 194-200 (1999); Simon et al., *Eur J Cardiothorac Surg* 23, 1002-1006 (2002); and Kasimir et al., *Tissue Eng.* 11:1274-1280 (2005)). Subsequent analysis of the valves indicated that the decellularization procedures had not been fully successful and that cellular debris and Gal antigen remained on the devices. The rapidity of structural valve deterioration (SVD) in this trial implicated an immune valve failure due to pre-existing Gal antibody. Gal is the major xenogeneic animal antigen, widely expressed in most mammals but not expressed in humans and Old World primates. Humans thus make Gal antibody in response to an organ, tissue, or cellular implant bearing Gal antigen. Compositions and methods are needed for antigen screening of organ, tissue, or cellular implants, using animal models matching the human immune system with regard to potential xenogeneic antigens.

SUMMARY

The first viable galactosyltransferase (Gal) knock-out sheep is described herein. The knock-out sheep comprise a deletion, insertion or mutation of alpha-1,3-galactosyltransferase (GGTA1) gene, a gene essential for Gal carbohydrate synthesis. This results in a break in protein synthesis of the GGTA1 gene. The viable Gal knock-out sheep is produced, for example, by fusing an enucleated sheep oocyte and a Gal knock-out sheep fibroblast. In some examples, the sheep is progeny of a Gal knock-out sheep produced by standard mating wherein the mutation of GGTA-1 is homozygous. The viable Gal knock-out sheep, upon contact of immune cells of the sheep with Gal, produces Gal antibodies. Thus, the viable Gal knock-out sheep can be used as a model implant recipient to detect Gal antigen present in a candidate biological implant.

Also provided herein is a novel method of screening a biological implant to determine whether the implant stimulates an antibody-mediated inflammatory response to Gal antigen. For example, the biological implant can be screened prior to clinical use. The method comprises providing a biological implant to be screened; implanting the biological implant into a recipient Gal knock-out animal and detecting evidence of antibody-mediated inflammatory response in the recipient Gal knock-out animal. If the recipient Gal knock-out animal shows signs of antibody-mediated inflammatory response, the biological implant is determined to express Gal antigen, and is thereby expected to induce a clinical anti-Gal antibody response that may compromise the effectiveness or durability of the implant in a human. The recipient Gal knock-out animal is selected from the group consisting of ovine, porcine, bovine, equine, canine, feline, and camelid.

In the methods provided herein, the biological implant can be any animal tissue or engineered animal product, including, for example, an organ, valve, blood vessel, conduit, mesh, powder, tissue (e.g., skin, bone, or vascular tissue), or a population of cells. Such an implant is optionally naturally occurring (e.g., from a donor animal of the same or different species as the recipient), decellularized, or engineered tissues, cells, organs, or proteins produced in vitro. In some methods, the biological implant is derived from a donor, for example, a donor Gal knock-out animal. Optionally, the recipient Gal knock-out animal is ovine and the donor Gal-knock out animal is porcine or bovine.

The detection step optionally comprises one or more of a radiologic, biochemical, immunologic, functional or histologic evaluation of the implanted biological implant; measuring Gal antibodies in a biological sample from the recipient Gal knock-out animal following implantation of the biological implant; testing the performance of the implant, for example, via echocardiography; evaluating implant calcification. By way of example, evaluating implant calcification can comprises radiologic evaluation of the implant in situ, or evaluating implant calcification comprises trace metal evaluation of the implant ex vivo.

Further provided is a method of implanting into a human subject a biological implant that has been screened according to the methods described herein. The method comprises screening a first biological implant according to any of the screening methods provided herein; detecting minimal or no signs of antibody mediated inflammatory response in the recipient Gal knock-out animal; and implanting a second biological implant into the human subject, wherein the second biological implant is comparable to the first biological implant. In other words, two implants from the same or similar source are used; one is screened and, if the recipient Gal knock-out animal that received the screened implant shows the absence of an antibody-mediated inflammatory response, the second is implanted into the human subject.

Although previous efforts have not resulted in a viable Gal-knock-out sheep, multiple methods can be used to make a viable galactosyltransferase (Gal) knock-out sheep comprising a deletion, insertion or mutation of the GGTA1 gene, for example, in the genetic reading frame of the GGTA1 gene. The genetic modification can be made by CRISPR/Cas, zinc finger nuclease, meganuclease, or TALENs technology, and optionally combined with either Somatic Cell Nuclear Transfer (SCNT or cloning) or direct zygote micromanipulation. By way of example, the method of making a viable galactosyltransferase (Gal) knock-out sheep comprising a deletion or mutation of a GGTA1 gene comprises fusing an enucleated sheep oocyte and a Gal knock-out sheep fibroblast to produce a knock-out sheep embryo; transferring the knock-out sheep embryo into an estrus synchronized recipient female sheep; allowing the recipient female sheep to carry the knock-out sheep to or near term; and collecting the viable galactosyltransferase (Gal) knock-out sheep. Optionally, the Gal knock-out sheep fibroblast is produced using RNA-guided nuclease editing. In some methods, the method further comprises breeding two viable galactosyltransferase (Gal) knock-out sheep to produce progeny galactosyltransferase (Gal) knock-out sheep.

BRIEF DESCRIPTION OF THE FIGURES

FIG. 2A shows Gal antibody-induced calcification. Calcium content of standard (black bars) and galactosyl transferase knockout (GTKO or GalKO) (open bars) glutaraldehyde fixed pericardium, 20 days after implantation, in 12-day old rats is shown. Significance was tested using a Student's t-test (p<0.05).

FIG. 2B shows calcification of formaldehyde-ethanol-Tween 80 (FET) anti-calcification treated standard (left column above GLUT fixation and GLUT+FET treated) and GTKO (right column above GLUT fixation and GLUT+FET treated) pericardium 30 days after subcutaneous rat implantation. A 30-fold (standard) to 330-fold (GTKO) reduction in calcification of Glut fixed tissue compared to Glut fixed and FET treatment was shown. Significance was tested using a Student's t-test (p<0.05).

FIG. 2C shows a significant increase in calcification due to human Gal antibody even after FET. Significance tested using a Student's t-test (p<0.05).

FIGS. 5A-J show Gal ELISA analysis of anti-Gal antibody expression in GalKO sheep (KO2102, white markers and bars) and wild type sheep (WT2106, black markers and bars). FIGS. A-D show Anti-Gal IgM in WT2106 and KO2102, at 1-4 months of age, respectively. FIGS. E-H show Anti-Gal IgG in WT2106 and KO2102, at 1-4 months of age, respectively. FIG. 5I is a summary of anti-Gal IgM, at 1-4 months of age, at a 1:160 serum dilution. FIG. 5J is a summary of anti-Gal IgG, at 1-4 months of age, at a 1:40 serum dilution.

FIG. 6A shows FACS analysis of Gal specific lectin GSIB-4 binding to HEK. HEK cells were stained with FITC conjugated GSIB-4 lectin (Vector Labs, (Burlingame, CA) FL-1201). HEK cells do not bind GSIB-4 and do not express the Gal antigen.

FIG. 6B shows FACS analysis of Gal specific lectin GSIB-4 binding to HEK Gal cells. HEK Gal cells were stained with FITC conjugated GSIB-4 lectin (Vector Labs, (Burlingame, CA) FL-1201). HEK Gal cells express the Gal antigen and strongly bind GSIB-4.

FIGS. 7A-F show analysis of sheep serum IgG reactivity (1:8 dilution) to HEK and HEK-Gal cells. FIGS. A-D show serum IgG binding to HEK (A and C) and HEK-Gal (B and D) cells at 6 months of age. FIG. 7A shows WT2106 serum IgG binding to HEK cells. FIG. 7B shows WT2106 serum IgG binding to HEK-Gal cells. FIG. 7C shows KO2102 serum IgG binding to HEK cells. FIG. 7D shows KO2102 serum IgG binding to HEK-Gal cells. FIG. 7E is a summary of IgG binding for GalKO sheep KO2102 at 3-6 months of age for IgG binding to HEK cells (black bars) and HEK-Gal cells (white bars). FIG. 7G is a summary of IgG binding for the wild type sheep WT2106 at 3-6 months of age. Differential positive IgG binding to HEK-Gal cells shows anti-Gal IgG specific reactivity.

FIG. 8A shows Gal-KO sheep KO2102 cytotoxicity at 6 months of age for HEK and HEK-Gal cells at serum dilutions of 1:8, 1:16 and 1:32.

FIG. 8B shows HEK-Gal cytotoxicity of purified human anti-Gal antibody (circles). A dilution series of purified human anti-Gal antibody was used to create a standard curve for Gal-specific cytotoxicity (dotted line). The cytotoxicity of sheep KO2102 (triangle) was mapped to this curve to derive an approximate estimate of anti-Gal antibody equivalent cytotoxicity. The dashed vertical lines indicate the equivalent levels of human anti-Gal IgG cytotoxicity (1.07, 0.87 and 0.26 µg/ml) for KO2102 at serum dilutions of 1:8, 1:16 and 1:32 serum dilution, respectively. When the dilutions are taken into account this corresponds to an equivalent cytotoxicity produced by human anti-Gal antibody of 8.5, 14.0 and 8.4 ug/ml (10.3±3.2 µg/ml, Mean±Std. Dev.). The coefficient of correlation ($R^2$) for the fitted logarithmic curve is 0.92.

DETAILED DESCRIPTION

Figure 1A:
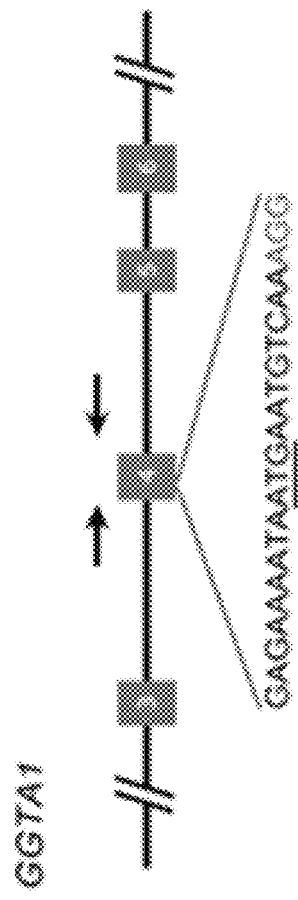
FIG. 1A is a schematic diagram of GGTA1 gene showing the position of the guide RNA (gRNA) sequence in exon 4. The GGAT1 translation start codon, ATG, is in the gRNA and is underlined. Arrows indicate location of PCR primers.

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

Currently, individuals who need a biological implant, such as a new heart valve, face difficult choices and uncertainty. By way of example, patients that require heart valve replacement can receive a mechanical heart valve (MHV), which requires continued, lifelong anticoagulation therapy with its attendant thrombotic, bleeding, and mortality complications, or a biological heart valve (BHV), which usually does not require long term anticoagulation therapy. BHVs continue to have limited durability from single ventricle heart defects, often necessitating one or more reoperations. Many of the uncertainties surrounding BHVs derive from premature structural valve degeneration (SVD). SVD, characterized by tissue calcification, leaflet tearing, and valve regurgitation and or stenosis, does not occur uniformly across all populations and is strongly age dependent. For patients less than 35 years old, there is up to 100% incidence of stenosis or regurgitation within 5 years after BHV surgery, compared to a 10% incidence within 10 years for patients over 65 years old. As described herein, the immune reaction between Gal Ab in valve recipients and Gal antigen in current BHVs promotes post-implantation valve calcification and SVD. The methods and compositions provided herein can be used to improve durability of a biological implant, for example, a BHV, by identifying a Gal-free implant. This greatly benefits implant recipients by delaying or avoiding reoperation, thereby increasing the utility of the biological implant.

Genetically Modified Sheep

Provided herein is a viable galactosyltransferase (Gal) knock-out (KO) sheep comprising a genetically modified Alpha-1,3-galactosyltransferase (GGTA1) gene, which is essential for synthesizing the Gal carbohydrate. In some genetically modified sheep, the genetic modification is a mutation in the nucleic acid encoding exon 4 of Alpha-1,3-galactosyltransferase. Set forth below, as SEQ ID NO: 1, is the wildtype nucleic acid sequence encoding Exon 4 and partial flanking intron sequences of the sheep GGTA1 gene. SEQ ID NO: 2 is a nucleic acid sequence encoding a mutated, i.e., genetically modified<exon 4 and partial flanking intron sequences of sheep GGTA1 gene in the Gal-KO sheep.

```
                                              (SEQ ID NO: 1)
TCCAGCTCTTTGCAACGCTATGGACTGTTGCCCACCGGACACTTCTGTC

CATGGAATTCTCCAGGCAAGAGTACTGGAGTGGGTTGCCGTGCCCTCCT

TCAGGGGGTCTTCTCCATCCAGGGATCGAACTTGCATCTCCTGCATTGC

AGGCGGATTCTCCACTGCTGAGCCCCTGGGGAAGCCCAGAACATGTGCC

TTAGCACTTGTTAAATATTCATCACCTTTTCCTTTTAGAAAGGACATAG

GTAGAAATAATTATTGAAAAAAATCATATCCCACTCTTGATATATTTAA

TCTATTTTCCCCCCTCTTCTTTTCTTTTCCCAGGAGAAAATAATGAA

TGTCAAAGGAAAAGTGATTCTGTCAATGCTGGTTGTCTCAACTGTCAT

CGTTGTGTTTTGGGAATATATCCACAGGTAATTATGGAACATGATAAAG

TGATGTTAATGAACGTCTCCATCAGCCAAGTCACCAGGTTGAATTGAAA

TTAGGACTTCTTCCTTCCTGTTTCCCTGAGCCCTA (SEQ ID NO: 2)
TCCAGCTCTTTGCAACGCTATGGACTGTTGCCCACCGGACACTTCTGTC

CATGGAATTCTCCAGGCAAGAGTACTGGAGTGGGTTGCCGTGCCCTCCT

TCAGGGGGTCTTCTCCATCCAGGGATCGAACTTGCATCTCCTGCATTGC

AGGCGGATTCTCCACTGCTGAGCCCCTGGGGAAGCCCAGAACATGTGCC

TTAGCACTTGTTAAATATTCATCACCTTTTCCTTTTAGAAAGGACATAG

GTAGAAATAATTATTGAAAAAAATCATATCCCACTCTTGATATATTTAA

TCTATTTTCCCCCCTCTTCTTTTCTTTTCCCAGGAGAAAATAATGAA

TGTAAAGGAAAAGTGATTCTGTCAATGCTGGTTGTCTCAACTGTCATCG

TTGTGTTTTGGGAATATATCCACAGGTAATTATGGAACATGATAAAGTG

ATGTTAATGAACGTCTCCATCAGCCAAGTCACCAGGTTGAATTGAAATT

AGGACTTCTTCCTTCCTGTTTCCCTGAGCCCTA
```

The targets of PCR primers for the amplification of the mutated region are underlined in SEQ ID NO: 1 and SEQ ID NO: 2 with double lines. The guide RNA (gRNA) sequence targeting exon 4 of GGTA1 is underlined with single line. The position of the starting codon, 'ATG', of GGTA1 in the target is depicted with larger font. Italicized letter (AGG) indicate the protospacer-adjacent motif (PAM). The nucleotide 'C' depicted with larger italic font in SEQ ID NO: 1 is deleted in SEQ ID NO: 2 (i.e., the mutated version of SEQ ID NO: 1), in the Gal-KO sheep (for example, in sheep #2101 and sheep #2102, described in the Examples).

As used herein, the term, viable, refers to a sheep that is born alive. In some cases, the sheep survives for a least five, six, seven, eight, nine, ten, eleven, or twelve months, or until the sheep reaches sexual maturity.

The GalKO sheep described herein are the first GalKO sheep to be viable, thus providing a clinically relevant GalKO sheep model for preclinical testing of a biological implant. Optionally, any of the GalKO sheep described herein produce Gal antibodies upon contacting the immune cells of the sheep with Gal antigen. Similar to humans, GalKO animals do not make the Gal antigen. Because they do not make the antigen, their immune system is capable of producing anti-Gal antibody. Typically these antibodies first develop early in life when the gastrointestinal tract is colonized by microfloral, as many species of bacteria express Gal antigen. This early Gal antibody is part of the natural antibody repertoire and is thought to provide protection from infection. The presence of this early anti-Gal antibody shows that the animal is devoid of the Gal antigen. Therefore, when a GalKO animal is challenged with a biological implant that has the Gal antigen, a strong anti-Gal immune response ensues.

As used herein, the term Gal-KO or GTKO sheep, refers to sheep with reduced levels of alpha-1,3-galactosyltransferase expression (for example, reduced mRNA and/or protein expression), such that the sheep does not produce functional alpha-1,3-galactosyltransferase enzyme in the Golgi apparatus and does not produce Gal antigen on the cell surface of cells in the sheep. Optionally, the GGTA1 gene is modified such that no transcription of the gene occurs. Optionally, the GGTA1 gene is modified such that no translation of the gene occurs. It is understood that a reduction in gene expression need not be complete, as the expression level of a gene can be reduced or decreased to varying degrees. For example, expression can be reduced by 100%, 99%, 95%, 90%, 85%, 80%, or 75% as compared to expression in an unmodified control.

A GGTA1 gene can be genetically modified using any method known in the art. For example, the gene can be modified by deletion, substitution, mutation, insertion, rearrangement, or a combination thereof. The modification can disrupt the gene such that transcription and/or translation of the gene is reduced. In some examples, an insertion can generate a stop codon in the middle of a gene, or shift the open reading from of the gene. In the Gal-KO sheep described herein, one or both alleles of the GGTA1 gene can be knocked out or inactivated. Therefore, homozygous knockouts where both alleles are inactivated as well as heterozygous knockouts where one allele is inactivated are provided herein.

Methods for making knockout transgenic animals, include, but are not limited to, oocyte pronuclear DNA microinjection, intracytoplasmic sperm injection, embryonic stem cell manipulation, somatic nuclear transfer, recombinase systems (for example, Cre-LoxP systems, Flp-FRT systems and others), zygote micromanipulation, zinc finger nucleases (ZNFs), transcriptional activator-like effector nucleases (TALENs), meganucleases, and RNA-guided gene editing systems (for example, clustered regularly interspaced short palindromic repeat/CRISPR/Cas systems, such as CRISPR/Cas9)). See, for example, Perisse et al. "Improvements in Gene Editing Technology Boost Its Applications in Livestock. Front Genet." 2020; 11:614688. Epub 2021 Feb. 20. doi: 10.3389/fgene.2020.614688; and Polejaeva, 25th Anniversary of Cloning by Somatic Cell Nuclear Transfer: Generation of genetically modified livestock using somatic cell nuclear transfer. Reprod Suppl. 2021; 162(1): F11-F22. Epub 2021 May 28. doi: 10.1530/REP-21-0072).

In some methods, a genetic modification is made to a somatic cell, for example, via CRISPR/Cas, TALENS, meganuclease technology etc. and the nucleus of the somatic cell is transferred to an enucleated egg of the same species. In some methods, the enucleated eggs or oocytes are used for somatic cell nuclear transfer, and then transferred to a surrogate mother. In some embodiments, genetically modified zygotes are transferred to a surrogate mother.

As used herein, the term TALEN means a protein comprising a Transcription Activator-like (TAL) effector binding domain and a nuclease domain and includes monomeric TALENs that are functional per se as well as others that require dimerization with another monomeric TALEN. The dimerization can result in a homodimeric TALEN when both monomeric TALEN are identical or can result in a heterodimeric TALEN when monomeric TALEN are different. TALENs have been shown to induce gene modification in immortalized human cells by means of the two major eukaryotic DNA repair pathways, non-homologous end joining (NHEJ) and homology directed repair. TALENs are often used in pairs but monomeric TALENs are known. A genetic modification made by TALENs or other tools may be, for example, chosen from the list consisting of an insertion, a deletion, insertion of an exogenous nucleic acid fragment, and a substitution. In general, a target DNA site is identified and a TALEN-pair is created that will specifically bind to the site. The TALEN is delivered to the cell or embryo, e.g., as a protein, mRNA or by a vector that encodes the TALEN. The TALEN cleaves the DNA to make a double-strand break that is then repaired, often resulting in the creation of an indel, or incorporating sequences or polymorphisms contained in an accompanying exogenous nucleic acid that is either inserted into the chromosome or serves as a template for repair of the break with a modified sequence.

In some methods, a TALEN-pair is introduced into a livestock cell or embryo that makes a genetic modification to DNA of the cell or embryo at a site that is specifically bound by the TALEN-pair, to the livestock animal from the cell. Direct injection may be used for the cell or embryo, e.g., into a zygote, blastocyst, or embryo. Alternatively, the TALEN and/or other factors may be introduced into a cell using any of many known techniques for introduction of proteins, RNA, mRNA, DNA, or vectors. Genetically modified animals may be made from the embryos or cells according to known processes, e.g., implantation of the embryo into a gestational host, or various cloning methods.

Zinc-finger nucleases (ZFNs) are artificial restriction enzymes generated by fusing a zinc finger DNA-binding domain to a DNA-cleavage domain. Zinc finger domains can be engineered to target desired DNA sequences and this enables zinc-finger nucleases to target unique sequences within complex genomes. By taking advantage of endogenous DNA repair machinery, these reagents can be used to alter the genomes of higher organisms. ZFNs may be used in method of inactivating genes. Materials and methods for using zinc fingers and zinc finger nucleases for making genetically modified animals are disclosed in, e.g., U.S. Pat. No. 8,106,255; U.S. 2012/0192298; U.S. 2011/0023159; and U.S. 2011/0281306.

The CRISPR/Cas9 system, an RNA-guided nuclease system that employs a Cas9 endonuclease, can be used to edit the genome of a host cell or organism. The CRISPR/Cas system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize an RNA-mediated nuclease, for example, Cas9, in complex with guide and activating RNA to recognize and cleave foreign nucleic acid. Guide RNAs having the activity of both a guide RNA and an activating RNA are also known in the art. In some cases, such dual activity guide RNAs are referred to as a single guide RNA (sgRNA).

As used herein, the term Cas9 refers to an RNA-mediated nuclease (e.g., of bacterial or archaeal origin or derived from a bacterial or archaeal nuclease). Exemplary RNA-mediated nucleases include the foregoing Cas9 proteins and homologs thereof. Other RNA-mediated nucleases include Cpf1 (See, e.g., Zetsche et al., Cell, Volume 163, Issue 3, p 759-771, 22 Oct. 2015), Cas13-based RNA editors, Cas-CLOVER (Li et al., Cas-CLOVER™: A High-Fidelity Genome Editing System for Safe and Efficient Modification of Cells for Immunotherapy. 2018 Precision CRISPR Congress Poster Presentation, Boston, MA) and homologs thereof.

Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chloroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi et al., *RNA Biol.* 2013 May 1; 10(5): 726-737; *Nat. Rev. Microbiol.* 2011 June; 9(6): 467-477; Hou et al., *Proc Natl Acad Sci USA* 2013 Sep. 24; 110(39):15644-9; Sampson et al., *Nature,* 2013 May 9; 497(7448):254-7; and Jinek et al., *Science* 2012 Aug. 17; 337(6096):816-21. Variants of any of the Cas9 nucleases provided herein can be optimized for efficient activity or enhanced stability in the host cell. Thus, engineered Cas9 nucleases are also contemplated. See, for example, Slaymaker et al., Rationally engineered Cas9 nucleases with improved specificity, *Science* 351 (6268): 84-88 (2016)).

By way of example, the viable Gal knock-out sheep is optionally or by fusing an enucleated sheep oocyte and a Gal knock-out sheep fibroblast, as described in the Examples. The method includes making a viable galactosyltransferase (Gal) knock-out sheep comprising a deletion or mutation of a GGTA1 gene comprising by fusing an enucleated sheep oocyte and a Gal knock-out sheep fibroblast to produce a knock-out sheep embryo; transferring the knock-out sheep embryo into an estrus synchronized recipient female sheep; allowing the recipient female sheep to carry the knock-out sheep to or near term; and collecting the viable galactosyltransferase (Gal) knock-out sheep. The Gal knock-out sheep fibroblast is optionally made using a gene editing method described above, for example, TALENs, ZNFs, or RNA guided gene editing. Optionally, the RNA-guided nuclease is Cas9.

Any of the knockout sheep produced using the methods described herein can be genotyped to identify the genetic modification of the GGAT1 gene and various genetic markers. For example, a genetic modification in the GGAT1 gene can be detected using standard techniques such as sequencing methods, PCR-based methods, and microchip analysis to name a few. In some cases, the genetic modification is in exon 4 of the GGAT1 gene. Exemplary primers for PCR detection of a modification in exon 4 include GGTA1-EXON4-Forward (TCCAGCTCTTTGCAACGCTA) (SEQ ID NO: 3) and GGTA1-EXON4-Reverse (TAGGGCTCAGGGAAACAGGA) (SEQ ID NO: 4), which can amplify a 522 base pair amplicon. Genotyping is a term that refers to the process of determining differences in the genetic make-up (genotype) of an individual by determining the individual's DNA sequence using a biological assay and comparing it to another individual's sequence or to a reference sequence. A genetic marker is a known DNA sequence with a known location on a chromosome. Selected genetic markers are consistently passed on through breeding, so the markers can be traced through a pedigree or phylogeny. Genetic markers can be a sequence comprising a plurality of bases, or a single nucleotide polymorphism (SNP) at a known location. Many markers are known and there are many different measurement techniques for correlating the markers to traits of interest or to establish a genetic value of an animal for purposes of future breeding or expected value.

Founder animals (F0 generation) can be produced by cloning and other methods described herein. The founders can be homozygous for a genetic modification, as in the case where a zygote or a primary cell undergoes a homozygous modification. Similarly, founders can also be made that are heterozygous. The founders may be genomically modified, meaning that the cells in their genome have undergone modification. Founders can be mosaic for a modification, as may happen when vectors are introduced into one of a plurality of cells in an embryo, typically after initial embryo cleavage. Progeny of mosaic animals may be tested to identify progeny that are genomically modified. An animal line is established when a pool of animals has been created that can be reproduced sexually or by assisted reproductive techniques, with heterogeneous or homozygous progeny consistently expressing the modification.

The knockout animals described herein include both progenitor and progeny animals. Progeny animals include animals that are descended from the progenitor as a result of sexual reproduction or cloning and that have inherited genetic material from the progenitor. Thus, the progeny animals comprise the genetic modification introduced into the parent. In some examples, the sheep is progeny of a Gal knock-out sheep produced by standard mating where the mutation of GGTA-1 is homozygous or the progeny of a sheep produced by fusing an enucleated sheep oocyte and a Gal knock-out sheep fibroblast. A knockout animal may be developed, for example, from embryonic cells into which the genetic modification has been directly introduced or from the progeny of such cells Animals that are produced by transfer of genetic modification (i.e., a GGAT1 gene knockout) through breeding of the animal comprising the genetic modification are also included. In some cases, two viable galactosyltransferase (Gal) knock-out sheep are bred to produce progeny galactosyltransferase (Gal) knock-out sheep. A cell or a population of cells from any of the knockout animals provided herein is also provided.

Screening Methods

As described in the Examples, the immune reaction in an implant recipient in response to Gal antigen in an implant promotes undesirable effect. For example, in the case of a heart valve implant with Gal antigen, the immune response post implantation results in valve calcification and SVD. (See, for example, O'Brien et al. (1999) and Simon et al. (2002)). There have also been isolated case reports of patients experiencing apparent allergic reactions after BHV implantation. One patient underwent 4 consecutive BHV replacement surgeries over a 7 month period with each successive valve developing blood culture negative endocarditis with occluding vegetative growth. (Fournier et al. *Lancet* 377:1542 (2011). Histology of each device showed an inflammatory eosinophilic infiltrate with vegetative growth. Between consecutive SBHV replacements the patient's serum showed increasing levels of anti-pork specific IgE consistent with an allergic reaction. Allergies specific to the Gal antigen are known to develop after inoculation by the lone star tick *Amblyomma americanum* and result in sensitization to mammalian meat products. (Commins et al., *J. Allergy Clin. Immunol.* 123:426-433 (2009). Mozzicato et al. (*J. Allergy Clin. Immunol. Pr.* 2:637-638 (2014) described 3 BHV patients with alpha-Gal allergy and elevated serum anti-Gal IgE. Two of these patients developed perioperative or postoperative allergic responses after SBHV implantation. Hawkins et al. (*Physiol. Behav.* 31:446-448 (2016)) described 2 cases in which BHV recipients developed alpha-Gal allergies from tick bites after BHV surgery. Each patient showed accelerated valve degeneration, which necessitated heart valve replacement with a MHV within 2 years of developing the Gal allergy. Although Gal allergies are rare, these case studies illustrate the pathogenicity of anti-Gal antibody and support a role for anti-Gal antibody dependent immune-mediated SVD. Therefore, the Gal antibody producing GalKO sheep described herein provide a useful model for screening prior to implantation a candidate biological implant or surrogate from the same or similar source.

Provided herein is a method of screening a biological implant for stimulation of an antibody-mediated inflammatory response to a Gal antigen. The method comprises providing a biological implant to be screened; implanting the biological implant into a recipient Gal knock-out animal; and detecting signs of an antibody-mediated inflammatory response in the recipient Gal knock-out animal (e.g., a Gal knock sheep made according to any method described herein.

As used herein, a biological implant can be a material (naturally occurring or engineered), tissue, organ, or cell, that is suspected of comprising a Gal antigen. These include fresh or frozen tissue, fixed animal tissue, cellular or acellular/decellularized tissue, tissue from a live donor or cadaver, and engineered tissue produced in vitro, to name a few. Any organ or tissue can be used for implantation. Such implants include, but are not limited to heart, lungs, glands, eye, stomach, spleen, pancreas, kidney, liver, intestine, uterus, bladder, skin, nerve, ears, nose, mouth, lips, gums, teeth, tongue, pharynx, esophagus, large intestine, small intestine, rectum, anus, pylorus, suprarenal capsule, bone, cartilage, tendon, ligament, skeletal muscle, smooth muscle, blood vessel, blood, trachea, ureter, urethra, ovary, oviduct, vagina, testes, seminal vesicles, lymph vessels, or any portion thereof.

In some methods, the implant is an organ, bone, skin, cell(s), blood vessel, ligament, mesh, bandage, patch, vascular conduit, stent, or valve, to name a few. In some methods, the biological implant is a heart valve or heart valve tissue. In some methods, the heart valve is a mitral valve, a tricuspid valve, a pulmonary valve, or an aortic valve. For example, and not to be limiting, the heart valve can be a fixed heart valve, a decellularized porcine or bovine heart valve, a heart valve made from a purified protein, or a heart valve made from a collagen matrix produced by in vitro cell culture (Syedain valves). Thus, the GalKO sheep described herein is useful for screening any form of heart valve implant.

In the screening methods provided herein, the recipient animal receiving the candidate implant is a Gal knock-out animal. The recipient Gal knock-out animal is selected from the group consisting of ovine, porcine, bovine, equine, canine, feline, and camelid. The biological implant is optionally derived from a donor animal, for example, a donor Gal knock-out animal. By way of example, the Gal knock-out recipient animal can be ovine and the donor animal can be porcine or bovine.

In the screening methods described herein, the antibody-mediated inflammatory response in the recipient Gal knock-out animal can be observed by various means. For example the response can be determined by detecting an increase in circulating Gal antibody in the recipient animal, an increase in Gal antibody binding to the implant, systemic complement activation in the presence of the implant, complement deposition on the implant, inflammatory cell infiltration of the implant, recovery of anti-Gal antibody from the implant after explantation or tissue calcification, to name a few.

The detection step optionally comprises one or more of a radiologic, immunologic, functional, or histologic evaluation of the implanted biological implant. In some methods, the detecting step comprises measuring Gal antibodies in a biological sample from the recipient Gal knock-out animal following implantation of the biological implant. In some methods, detecting comprises testing the performance of the implant. In some methods, detecting comprises evaluating implant calcification. In some methods, evaluating implant calcification comprises radiologic evaluation of the implant in situ. In some methods, evaluating implant calcification comprises evaluation of the implant ex vivo, for example, by performing a biochemical trace metal evaluation. In some methods, histologic evaluation comprises detecting infiltrating immune cells, for example, cytotoxic T cells, mediated by an increase in the production of Gal-specific antibodies.

Implantation Methods

Further provided is a method of preclinical testing of a biological implant prior to clinical use into a human subject. The method comprises screening a biological implant according to any of the screening methods provided herein and detecting minimal or no sign of antibody-mediated inflammatory response in the recipient Gal knock-out animal. In some methods, the biological implant is derived from animal tissue expressing Gal. For clinical use, with respect to the Gal antigen, a biological implant exhibiting minimal or no signs of antibody-mediated inflammatory response in the recipient Gal knock-out animal in a screening method described herein can be implanted into the human subject.

Further provided is a method of implanting a biological implant into a human subject. The method comprises screening a first biological implant according to any of the screening methods provided herein; detecting minimal or no sign of antibody mediated inflammatory response in the recipient Gal knock-out animal; and implanting a second biological implant into the human subject, wherein the second biological implant is comparable to the first biological implant. Comparable to, as used herein, means that the implant is derived from the same or similar source, for example, from the same animal or from an animal with the same genetic profile.

A biological implant exhibiting minimal or no signs of antibody-mediated inflammatory response in the recipient Gal knock-out animal in a screening method described herein can be implanted into the human subject. As used herein, implanting includes, but is not limited to, administering, introducing, applying, injecting, grafting (e.g., bone or skin), suturing, and inserting the implant into the human subject. The biological implant may be implanted by a method or route which results in localization of the biological implant at a desired site. Tissues or cells can be implanted in a subject by any appropriate route that results in delivery of the tissue or cells to a desired location in the subject where at least a portion of the tissue or cells remain viable. In some embodiments, at least about 10%, 20%, 30%, 40%, 50%, 60%, 70%, 80%, 90%, or 100% of the cells (whether administered separately or as part of a tissue or organ) remain viable after administration to the subject.

As used throughout, by human subject is meant an individual. The subject can be an adult subject or a pediatric subject. Pediatric subjects include subjects ranging in age from birth to eighteen years of age. Optionally, the subject can be a subject diagnosed with a condition requiring an implant.

In some methods, the recipient Gal knock-out animal is ovine. In some methods, the first and second biological implants comprise no detectable Gal antigen. In some methods, the first and second biological implants are organs, tissues or cells. In some methods, the biological implants are derived from a second Gal knock-out instead of Gal positive animal tissues, organs, or cells. Optionally, the second Gal knock-out animal is porcine.

Any of the implantation methods provided herein can optionally, further comprise administering immunosuppressive therapy to the subject. Exemplary immunosuppressive agents include, but are not limited to, cyclosporine, prednisone, tacrolimus, sirolimus, azathioprine, methotrexate, mycophenolate and FK506.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Generation of GGTA1−/− Male Fetal Fibroblasts Using CRISPR/Cas9

Sheep fetal fibroblasts (SFF) from domestic sheep (*Ovis aries*) were used in this study since they are the cells of choice for production of genetically engineered sheep by somatic cell nuclear transfer (SCNT). Specific PCR primers were designed according to sheep GGTA1 genome sequences (GenBank, NC_040254.1) (GGTA1-EXON4-F: TCCAGCTCTTTGCAACGCTA (SEQ ID NO: 5)); GGTA1-EXON4-R: TAGGGCTCAGGGAAACAGGA (SEQ ID NO: 6)) and used to amplify exon 4 and partial intron flanking sequences (522 bp). A gRNA (GAGAAAATAATGAATGTCAA) (SEQ ID NO: 7) was designed to target exon 4 of the GGTA1 gene (FIG. 1A).

Figure 1B:
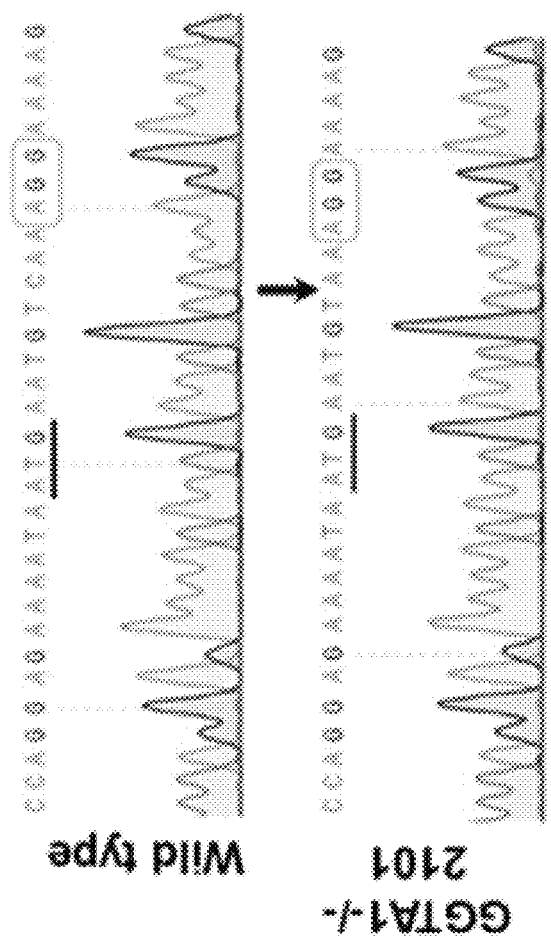
FIG. 1B shows a representative sequence analysis for GGTA1−/−F0 lambs.

SFFs were transfected with the gRNA and Cas9 protein compound using an electroporation-based method and gene mutation efficiency was determined by PCR/T-vector cloning assays 3 days after transfection. Single-cell-derived fibroblast colonies were isolated by limiting dilution of cells transfected with the gRNA and screened by PCR and Sanger sequencing (FIG. 1B). Targeted biallelic disruption of GGTA1 was achieved in 10/26 colonies (38.5%).

Generation of GGTA1−/− Sheep by SCNT

Figure 1C:
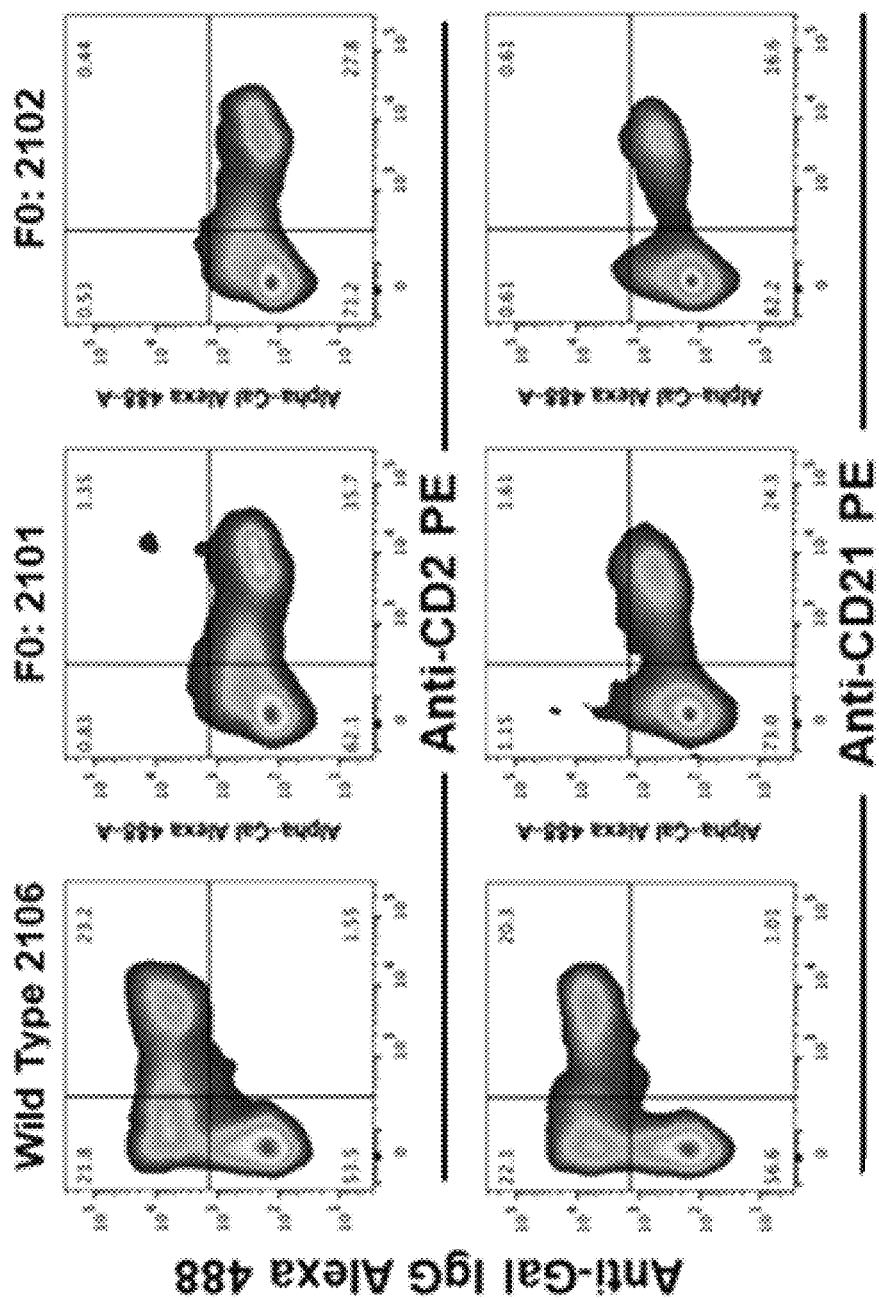
FIG. 1C shows a FACS analysis of peripheral blood mononuclear (PBMNC) from wild type and 2 healthy GGTA−/− sheep (2101 and 2102). Approximately 41% of the PBMNC in wild type sheep were Gal positive with CD2 positive α/β T cells and CD21 positive B cells. The two GGTA1 knockout sheep do not express Gal but have normal T and B cell profiles.

Four GGTA1−/− male colonies were used as donor cells for SCNT. In total, 130 cloned embryos were transferred into 10 estrus-synchronized recipient ewes. Five pregnancies were initially confirmed by ultrasonography at Day 40-45 of gestation. Four of them developed to term (4/10, 40%). One lamb was stillborn (#2104), and another (#2103) died within 48 h after delivery due to Large Offspring Syndrome (LOS) commonly observed in cloned sheep. Two GGTA1−/− lambs, #2101 and #2102 (FIG. 1C), were successfully produced. They are currently 1.9 months old and appear healthy. Genotyping results indicated that all cloned lambs carried the same mutations as those of the donor cells from which they originated. Flow cytometry staining of peripheral blood mononuclear cells from wild type and the 2 GGTA−/− founder lambs 2101 and 2102 show a complete loss of Gal expression in the GalKO sheep (FIG. 1C).

Commercial Valve Antigenicity and Gal Antibody-Induced Calcification

In the rat and rabbit subcutaneous implant models, the human anti-Gal IgG increases calcification of standard, but not GalKO pig, pericardium (FIG. 2A). Anti-calcification treatment reduced calcification levels in standard and GalKO pericardium as expected (FIG. 2B) but did not prevent anti-Gal Ab induced calcification (FIG. 2C), showing that passive physiochemical tissue calcification and immune-mediated calcification are independent processes. This was the first experimental identification of a clinically plausible source of BHV-specific Ab that could initiate an immune-mediated inflammatory response to promote calcification and SVD.

Manufacture of GalKO BHVs

Porcine pericardial BHVs from both standard and GalKO glutaraldehyde fixed pig pericardium have been produced for years. These valves are the product of years of in vitro testing, comparing the morphology, biochemistry and tensile properties of standard and GalKO pericardium, iterative BHV engineering designs, manufacturing optimization, and hydrodynamic and accelerated wear testing. This developmental process has successfully created a new pericardial BHV design, which is durable, has excellent hydrodynamic performance, and achieves clinical regulatory standards. Therefore, a high quality valve vehicle is available to test the two types of pig pericardium (standard and GalKO) for the effects of anti-Gal Ab on tissue calcification. This genetic engineering approach to creation of GalKO BHVs is superior to the chemical (alpha-galactosidase) method as it is more complete, consistent and predictable.

Analysis of BHVs in Juvenile Sheep

Figure 3A:
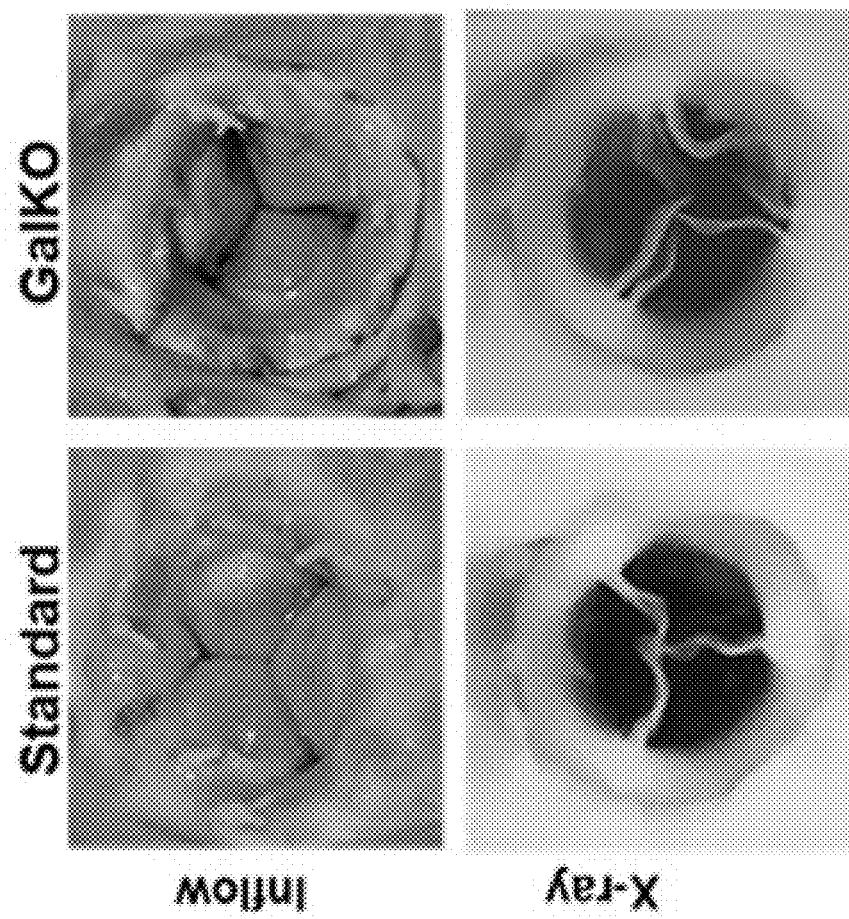
FIG. 3A shows explanted photographs of the inflow surface (top) and Faxitron x-rays (bottom) of BHVs 90-days after mitral valve implantation in juvenile sheep.
Figure 3B:
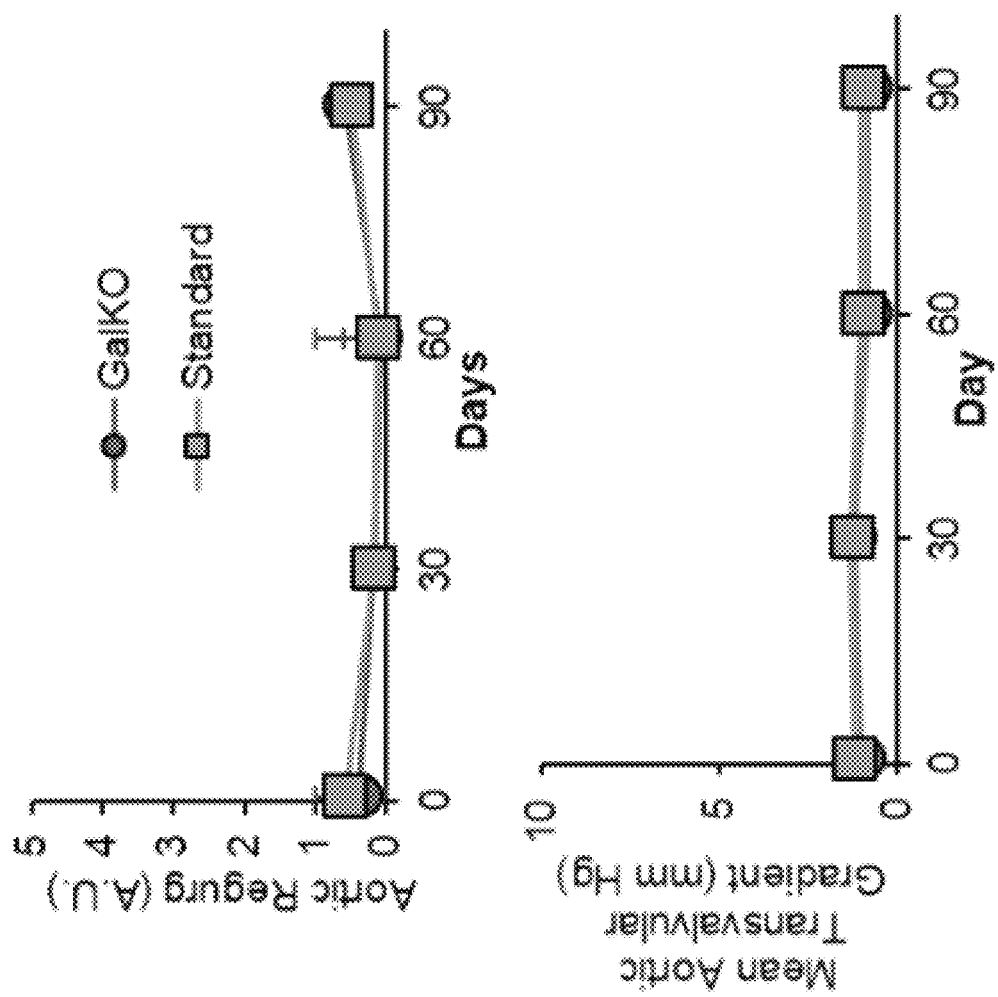
FIG. 3B shows mean aortic regurgitation (top) and mean aortic transvalvular gradients (bottom) for BHVs made of GalKO (n=5) and Standard (n+4) pig pericardium. Error bars are standard deviation. There was no significant difference between the tissue types.
Figure 3C:
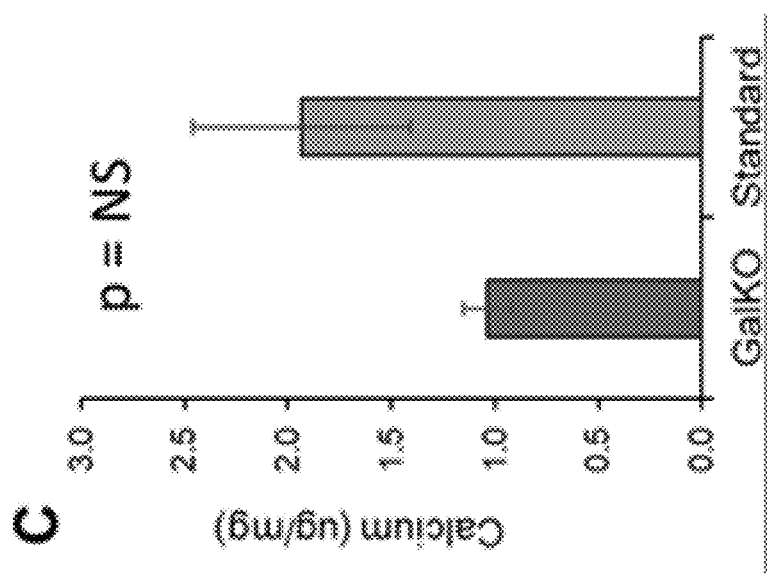
FIG. 3C shows there was no significant difference in tissue calcification during the study period or at explant.

Both standard or GalKO BHVs were used in an adolescent sheep mitral valve implant study, initially for 48 hours, and more recently for 90 and 150-days to compare hemodynamic function, thrombogenicity, and the biological equivalence of both types of BHV tissues. These adolescent sheep studies compared the tissue-specific effects of BHV implantation on recipient survival and health and on valve hemodynamic performance (effective orifice area, leaflet motion, regurgitation, and transvalvular gradient pressure), pathology including thrombus deposition, pannus formation, and tissue calcification. Twenty-one of twenty-two valves completed these studies and performed normally with no valve-related deaths. There were no differences in valve pathology (FIG. 3A), hydrodynamic performance (FIG. 3B), or tissue Cal (FIG. 3C) during the study period or at explant. In addition to showing the biological equivalence of both Gal positive and negative BHVs, these studies validate BHVs. These same analytical methods and study criteria, in addition to the immune analysis discussed below, are the core techniques used to characterize recipient health, valve pathology, and tissue Cal. This time period of implantation meets FDA criteria for clinical application.

Immunobiology of Innate Anti-Gal Antibody

Figure 4:
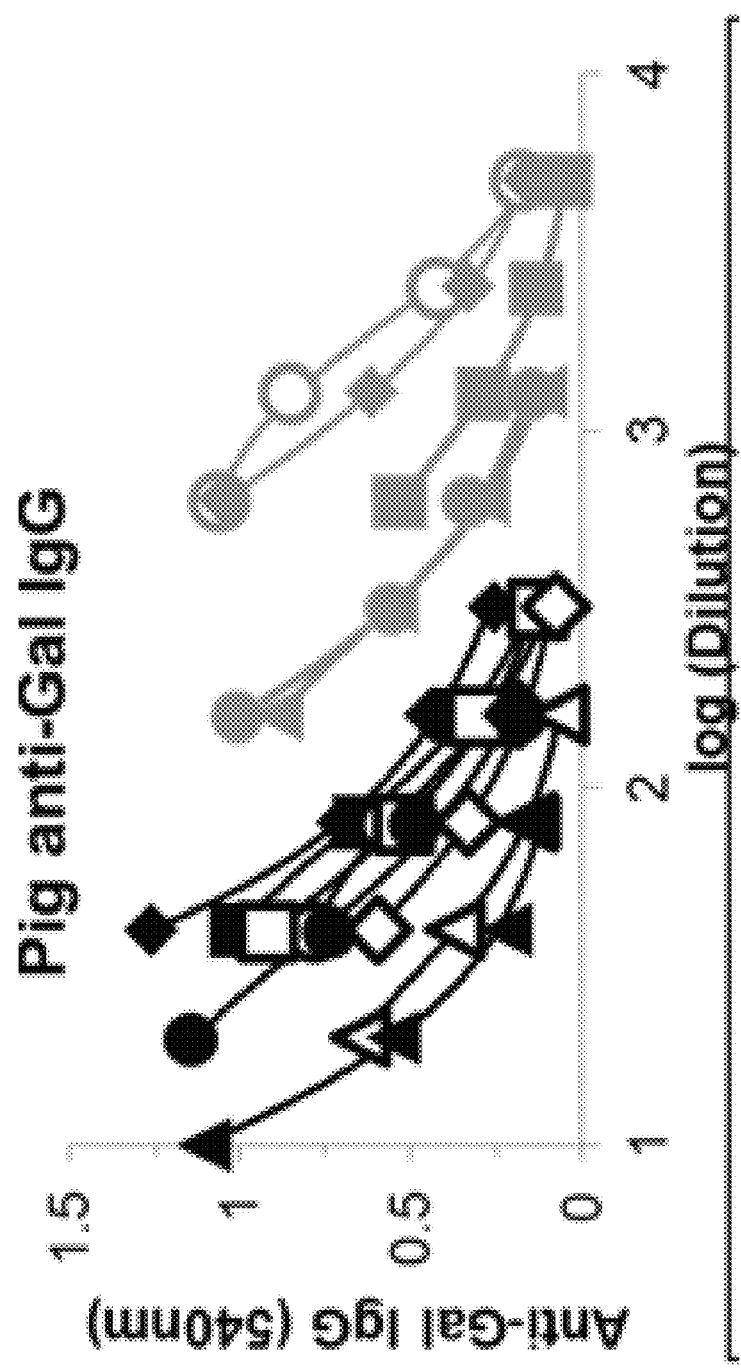
FIG. 4 shows anti-Gal antibody expression in GTKO pigs. Anti-Gal antibody is evident from 2-3 months of age (black, n=8) and remains present thereafter ((curves on right side of graph between 3 and 4 of X axis) 2-3 years of age, n=5).

Humans, nonhuman primates, and genetically engineered mice and pigs that lack the Gal antigen all spontaneously produce anti-Gal antibody as part of the natural antibody repertoire. These anti-Gal Abs develop after birth in response to microfloral stimulation. In pigs it was found that anti-Gal antibodies are evident beginning at 2 months of age (FIG. 4) and remain in circulation thereafter. Others report GalKO porcine anti-Gal antibodies to reach peak levels by 3 months of age. Genetically engineered GalKO animals thereby model human anti-Gal Ab expression. The GalKO sheep produced in this study are unique.

Generation of GGTA1−/− Sheep by Somatic Cell Nuclear Transfer (SCNT) and Breeding Fetal fibroblasts from GGTA1−/− male colonies are used as genetic donors for SCNT to enucleated mature oocytes by micromanipulation. Individual GGTA1−/− somatic cells inserted into the perivitelline space are fused with enucleated oocytes using double electrical pulses of 1.6 KV cm-1 (20 μsec each). Reconstructed embryos will be activated by ionomycin (5 min), and 6-DMAP and cycloheximide treatments. Cloned embryos will be cultured in vitro in SOF medium for approximately 12 h and then transferred into synchronized recipient females. Each of the GGTA1−/− animals will be genotyped by sequencing the mutation sites to confirm the presence of biallelic mutation.

Genotype and Phenotype of Cloned Sheep

The genotype and phenotype of cloned sheep is determined from fresh frozen and formalin tissue biopsies. Genomic DNA is produced from fresh frozen tissue by protease K tissue digestion and phenol/chloroform extraction. The genomic GGTA-1 exon 4 region flanking the sgRNA sites is amplified using Platinum SuperFi Green PCR mix (Thermo Fisher Scientific, Waltham, MA) and exon 4 primers GGTA1-EXON4-F (TCCAGCTCTTTGCAACGCTA) (SEQ ID NO: 3) and GGTA1-EXON4-R (TAGGGCTCAGGGAAACAGGA) (SEQ ID NO: 4). The amplified product is cloned into pCR Blunt II TOPO plasmid for Sanger sequencing. For each cloned animal, at least 10 independent sequences are analyzed to insure detection of mutation(s) on both alleles. Formalin fixed tissue is embedded in paraffin, sectioned, and stained with horseradish peroxidase conjugated GSIB-4 in the presence and absence of 10 mM free alpha-Gal trisaccharide, to measure Gal-specific tissue expression. Paraffin sections of standard and GalKO porcine tissue is co-stained with the sheep samples as positive and negative controls.

Analysis of Innate and Adaptive Sheep Anti-Gal Ab Reactivity

Anti-Gal innate and adaptive humoral immunity was analyzed in the existing GalKO sheep Similar studies are used to analyze anti-Gal innate and adaptive humoral immunity in all recipient sheep (prior to and after BHV implantation).

Anti-Gal Ab was assessed by (1) a Gal ELISA method; (2) a complement dependent cytotoxicity (CDC) assay measuring GalKO sheep serum cytotoxicity; and (3) a quantitative Flow cytometry analysis of sheep IgG and IgM binding to GalKO and standard PAECs.

Spontaneous Production of Anti-Gal Antibody in GalKO Sheep

A standard Gal ELISA (Byrne et al. "Evaluation of different alpha-Galactosyl glycoconjugates for use in xenotransplantation," *Bioconjug Chem* 2002, 13(3):571-581), used for analysis of human and nonhuman primate serum, was modified to analyze sheep serum. The ELISA format uses Gal-conjugated human serum albumin (HSA-Gal, Dextra Laboratories (Reading, United Kingdom), Cat #NGP2334), HSA coated plates, and horse radish peroxidase conjugated rabbit anti-sheep IgM (Bethyl Laboratories (Montgomery, TX), Cat No. A130-109P) or rabbit anti-sheep IgG (Bethyl Laboratories, Cat No. A130-201P) detection antibody. Sheep serum was diluted two-fold (range 1:20 to 1:10,240) in ELISA buffer (phosphate buffered saline (PBS) containing 1% HSA and 0.1% Tween 20), and incubated in ELISA plate wells coated with either HSA-Gal or HSA at 4° C. for 90 minutes. The plates were washed with PBS containing 0.1% Tween 20 and incubated with anti-sheep IgM or IgG for 60 minutes at room temperature. Antibody binding was detected measuring the optical density at 450 nm after incubation with 3,3',5,5'-tetramethylbenzidine (TMB) color substrate. The anti-Gal ELISA was designed to analyze matched sets of wild type and GalKO serum samples, on the same ELISA plate, from months 1-4. This insures that the results from wild type and GalKO serum are comparable. Data for GalKO sheep KO2102 and wild type sheep WT2106 is shown in FIGS. 5A-J. Specific anti-Gal reactivity was determined as the difference between binding to HSA-Gal and HSA coated wells.

The ELISA analysis shows the progressive evolution of serum anti-Gal IgM (FIG. 5A-D) and IgG (FIG. 5E-H) in sheep KO2102 and the absence of anti-Gal antibody in WT2106. Anti-Gal IgM is evident beginning in month 2 (FIG. 5B) and increases in months 3 and 4 (FIGS. 5C and D). At a 1:160 serum dilution, there is a progressive increase in anti-Gal IgM reactivity in KO2102 serum with little reactivity (OD450<0.05) in serum from the WT sheep WT2106 (FIG. 5I). The anti-Gal IgG analysis (FIG. 5E-H) shows a similar result, with the first very weak indication of anti-Gal IgG beginning in month 2. At a 1:40 serum dilution there is a progressive increase in anti-Gal IgG reactivity in KO2102 serum with little reactivity evident in serum from the sheep WT2106 (FIG. 5J).

Analysis of Antibody Reactivity to HEK and HEK-Gal Cells

Human embryonic kidney cells (HEK293) and HEK293-Gal cells were used to measure anti-Gal IgG reactivity in serum samples from months 3-8. The HEK293 cell line is an O-Blood group human cell line that does not express the Gal antigen and does not bind the Gal-specific lectin *Griffonia simplicifolia* (GSIB-4) (FIG. 6A). In contrast, HEK293-Gal cells express the porcine GGTA1 gene and produce abundant levels of Gal antigen which binds high levels of GSIB-4 lectin (FIG. 6B). These cell lines are advantageous for this analysis because they only differ by expression of the Gal antigen. Sheep antibody that binds to HEK-Gal cells, but does not bind to HEK cells represents anti-Gal specific antibody.

For the analysis of sheep IgG binding to HEK293 and HEK293-Gal cells, sheep serum (1:8 dilution) was incubated with 200,000 cells in FACS buffer (PBS with 2% HSA and 5% Donkey serum) at 4° C. for 45 minutes. Antibody binding was detected using a Dylight488 conjugated Donkey anti-Sheep IgG antibody (BioRad (Hercules, CA), STAR88D488GA). Samples were analyzed on a Becton Dickson BD FACSCanto II cytometer using FACS Diva software. As in the Gal ELISA described above, each analysis compared a set of GalKO and WT serum samples in parallel.

At six months of age, serum from WT2106 showed only low levels of reactivity to both HEK293 (FIG. 7A) and HEK-Gal cells (FIG. 7B). The GalKO KO2102 serum similarly shows low reactivity to HEK cells (FIG. 7C) but much higher reactivity to HEK293-Gal cells (FIG. 7D) indicating Gal-specific IgG. Across the 3-8 month serum samples, the GalKO KO2102 serum consistently shows greater reactivity to HEK-Gal cells compared to HEK293 cells (FIG. 7E). At six months of age, there was 16.5-fold greater IgG binding of GalKO KO2102 IgG to HEK293-Gal compared to HEK293 cells. The WT2106 serum showed variable, generally low, reactivity between the HEK293 and HEK293-Gal cell lines (FIG. 7F) indicating that, compared to anti-Gal antibody, WT sheep serum has relatively little IgG reactivity to these human cells.

Cytotoxicity of Sheep Anti-Gal Antibody

The immune mechanism for structural valve degeneration (SVD) suggests that tissue calcification is enhanced by antibody binding to the tissue. This antibody binding to valve tissue initiates a protracted inflammatory cycle involving complement fixation and macrophage recruitment leading to oxidative and proteolytic tissue injury. This injury opens up the tissues allowing more antibody binding, complement fixation, macrophage recruitment and tissue injury. This progressive tissue injury enhances the rate of tissue calcification through a myriad of passive and active calcification processes. Moreover, the immune injury produced by anti-Gal antibody is mediated by the fixation of complement on the implanted tissue. Complement fixation amplifies the impact of antibody binding by fixing complement components to the tissue surface and producing anaphylatoxins (C5a, C3a). These small peptides are released into circulation and attract macrophages and other inflammatory cells to the site of complement fixation. Macrophages bind to the implanted tissue through Fc-receptors which bind the Fc portion of antibody. By engaging the antibody/complement complex through Fc-receptors the macrophages are activated and produce proteases and free oxygen radicals which damage the implanted tissue and attracts further inflammatory cells. Therefore, it is important that anti-Gal antibody produced by GalKO sheep is cytotoxic and capable of complement activation.

A complement mediated lysis assay was used, with HEK293 and HEK293-Gal cells, to determine if sheep anti-Gal antibody is cytotoxic (Sharma et al. "Pig cells that lack the gene for alpha1-3 galactosyltransferase express low levels of the gal antigen," Transplantation 2003, 75(4):430-436). This standard complement dependent lysis assay detects complement induced cell lysis by the incorporation of the fluorescent dye propidium iodide which is normally excluded from cells with undamaged cell membranes. This assay begins with an antibody labelling phase where 100,000 HEK and HEK-Gal cells are incubated at 4° C. for 45 minutes with either purified human anti-Gal IgG antibody or serial dilutions of sheep serum (6 month sample with 1:8, 1:16 and 1:32 dilutions). In the second phase, the cells are washed and then incubated at 37° C. for 90 minutes with 10% baby rabbit complement. If the cells have complement fixing antibody bound to their surface, that antibody will initiate the complement cascade resulting in the formation of membrane attach complexes which breach the cell membrane. After the incubation with complement, the cells are stained with propidium iodide (PI), which stains the nuclei of cells with compromised cell membranes. The cells are immediately analyzed for PI incorporation using a BD FACSCanto II flow cytometer. Cell lysis is based on the percentage of cells with PI+ staining. Purified human anti-Gal IgG (a 2-fold dilution series from 2 µg/ml to 15.6 ng/ml) was used to establish a standard cytotoxicity curve. This curve was used to gauge the relative cytotoxicity of sheep serum antibody to known amounts of human anti-Gal IgG.

At 6 months of age, serum from GalKO sheep KO2102 had a high degree of cytotoxicity to HEK-Gal cells (FIG. 8A). At a 1:8 serum dilution, 48% of HEK-Gal cells were lysed by serum from KO2102, compared to 0.4% of HEK cells. The cytotoxicity of KO2102 serum decreased to 30% at a 1:32 dilution. When the cytotoxicity of KO2102 serum was mapped to the human anti-Gal IgG standard (FIG. 8B, triangles), and the serum dilutions are accounted for, sheep serum cytotoxicity equivalent to 8.5, 14.0 and 8.4 µg/ml of human anti-Gal antibody was observed, at 1:8, 1:16 and 1:32 dilution respectively.

The results of the ELISA, flow cytometric analysis of IgG staining of HEK293 cells HEK-Gal cells, and cyotoxicity studies showed that GalKO sheep spontaneously produce anti-Gal antibody, which is not present in standard, wild type (WT) sheep Adaptive Anti-Gal Ab Response The adaptive anti-Gal Ab response of the existing GalKO sheep will be tested in year 1 after immunization with a Gal-conjugated Keyhole limpet hemocyanin (Gal-KLH) Ag. This Gal-KLH Ag will be used to immunize nonhuman primates. Serum samples will be obtained prior to primary immunization, at 2 week intervals after each booster immunization and at 1 and 2 months after the last booster immunization. These samples from existing sheep and post BHV implant samples from SA2 will be analyzed by ELISA, CDC and quantitative flow cytometry.

BHVs for Implantation

BHVs are produced with 0.6% glutaraldehyde fixed standard pericardium (Group A) or GalKO pericardium (Group B) as previously described (Rahmani et al. (2019) A Durable Porcine Pericardial Surgical Bioprosthetic Heart Valve: a Proof of Concept. J Cardiovasc Transl Res 12, 331-337. The valves are further treated with a well-recognized clinical anti-mineralization process using a combination of formalin, ethanol and Tween 80 (Carpentier et al. (1984) Techniques for prevention of calcification of valvular bioprostheses. Circulation 70, 1165-1168. This treatment, known to minimize passive tissue calcification, should improve detection of immune mediated Gal antibody dependent tissue calcification and SVD. Sheets of 0.6% glutaraldehyde fixed pericardium were treated for 2 hours in a buffered solution of 4% Formalin, 22% Ethanol and 1.2% Tween 80 (FET) (U.S. Pat. No. 7,214,344 B2), washed with sterile saline and stored in 0.2% glutaraldehyde until used for valve construction. Valves were constructed as described by Rhamani et al. (2019). Post construction valves were treated with FET for 2 hours, washed with sterile saline, sterilized in 0.6% glutaraldehyde for 2 hours and stored in 0.2% glutaraldehyde until implantation.

Mitral Valve Implantation

GalKO sheep are acclimatized for 1 week prior to surgery. Experimental Surgical Services (ESS), is a preeminent valve testing service used extensively by commercial BHV manufacturers. ESS is AAALAC accredited, fully compliant with USDA's Animal Welfare Act and for performing research under the FDA's Good Laboratory Practice regulations. ESS works closely with the Research Animal Resources (RAR) division of the University of Minnesota, which provides all research animal health screening, perioperative feed and care. Mitral valve implantation is performed through a left lateral thoracotomy using standard surgical procedures. An implantation age of 6 months is expected to provide a good match between the recipient mitral annulus and the 25 mm valves that are produced. Prior to implant, echocardiography is used to image the mitral annulus to insure good size matching. Postoperatively recipients are maintained at the ESS facility and observed daily by veterinarian staff for up to 14 days to ensure complete recovery before transport to the University Northbound Farm where the animals are monitored bi-weekly by a veterinarian and twice daily by ESS personnel. Weekly body weight and temperature checks are performed and recipient blood and serum samples are collected prior to surgery and at 1 week, and monthly intervals post-surgery. Blood samples are analyzed by routine clinical tests for complete blood counts, coagulation (fibrinogen, prothrombin ratio (PR) and activated partial thromboplastin time (aPTT)), clinical blood biochemistry (Glucose, Creatinine, Urea, Calcium, Chloride, Sodium, Potassium, Bicarbonate, Phosphorus, Plasma Proteins, Magnesium, Total Bilirubin, Gamma Glutamyl Transferases, Aspartate Aminotransferase (AST), Alanine Aminotransferase (ALT) and Alkaline Phosphatase) and hemolysis (Plasma Free Hemoglobin) to monitor recipient health. Serum samples are also analyzed. BHV function is monitored by transthoracic echocardiography performed on the day of surgery and at 30, 90 and 150 days after surgery.

Results and Interpretation

The surgical pericardial BHVs that are produced should have in vitro durability consistent with the regulatory performance standards set for a new clinical BHV. A 90-day mitral valve replacement in wild-type juvenile sheep study to determine biological equivalence between standard and GalKO pericardium was completed. In this study, nine out of ten recipients completed the study protocol and no valve failures occurred in any recipients. Regardless of tissue type, all valves showed excellent and equal hemodynamic function with minimal thrombosis and tissue calcification.

Analysis of all Sheep Recipients

Animal health, valve performance and immune responses in vivo as well as detailed valve pathology relevant to calcium content and SVD, after explantation of the BHVs, and after 150 days implantation are analyzed. These analyses identify any differential effect between Group A (Gal antigen positive) or Group B (Gal antigen negative) BHVs on recipient GalKO sheep health and immune responses. These studies allow comparison of implanted valve performance, in vivo, and detailed pathology and calcification after 150 days implantation.

Experimental Design

The overall design of this study is modeled on the regulatory guidelines for preclinical testing of new BHVs. This includes an extended 150-day study period which is effective for distinguishing marginal valve performance, and in this case provides a longer timeframe in which to develop I-M BHV calcification and SVD. At completion of the study (150 days) recipients are anesthetized and infused with Heparin (2 mg/kg IV). Before euthanasia, contrast cardiac angiography is performed to detect any valvular insufficiency. Cardiac pressures and outputs are measured. An epicardial ultrasound is performed to document terminal valve performance. Standard blood tests are analyzed. Each animal is euthanized under anesthesia by an approved protocol. The BHV implant is exposed. Prior to explant, tissue integration and positioning of the valve, mechanical tears, macroscopic calcification, thrombus and evidence of cardiac abrasion are recorded by digital photography. After explant, gross morphology of the inflow and outflows aspects of the valve looking for pannus, thrombus and leaflet damage, is similarly documented. Thrombus formation for each valve is scored for the extent and size of adhered and non-adhered external thrombus (0=non-existent or minimal, 1=minimal covering 1-25% of surface area, 2=moderate covering 26-50% of surface area, 3=severe covering 51-75% of surface area and 4=extensive covering 76-100% of surface area). The valve is preserved in formalin for further analysis. A full recipient necropsy is performed at termination and for any recipient that dies before 150 days. The necropsy includes histology of recipient heart, lung, liver and kidney. Valve related death/complications are analyzed using a Fisher's exact test. Ordinal mean thrombus scoring for each group is analyzed by a Kruskal-Wallis H test.

Radiology, histology and most immunohistochemical processing and scoring of the explanted valves is performed by Alizee Pathology (Thurmont, MD). Quantitative analysis of calcium for each valve is performed by Legend Technical Services (St. Paul, MN). Immunohistology to further measure valve inflammation is performed in the laboratory using paraffin sections prepared by Alizee Pathology. Each analysis, radiology, histology, immunohistology, quantitative calcium analysis and echocardiography is performed in a blinded manner.

Valve Radiology and Histology

A high resolution digital radiograph is made of the inflow, outflow, and 2 orthogonal lateral views of the valve to identify and localize radiodense areas indicative of tissue calcification. Radiographs for each leaflet are evaluated semi-quantitatively by a staff pathologist with the following grading system: 0=absent, 1=Focal, pin-points <1 mm diameter, 2=Focal, >1 mm or multiple pin-point spots, 3=multiple spots >1 mm and 4-massive deposition. An average score for each valve is calculated from the results of each of the 3 leaflets.

For histology, each leaflet of the valve (left coronary, right coronary and non-coronary) is excised from the BHV and trimmed to produce a central strip, approximately 2 mm wide, running the length of the leaflet from the adherent margin to the free edge. This area is embedded in paraffin and 5 micron longitudinal cross sections are cut and stained with Hematoxylin-Eosin (H+E), Gomori's Elastin Trichrome (GET) and Von Kossa (VK). These standard histology stains are evaluated overall inflammation and inflammatory cell types (polymorphonuclear cells, lymphocytes, plasma cells, eosinophils, macrophages, giant cells); the presence of pannus or thrombus; and areas of calcium deposition. Paraffin sections of each valve are stained by immunohistochemistry to detect deposition of IgM, IgG, complement C1q and infiltration of leukocytes (CD45), lymphocytes (CD3), T-cells (CD8) and B-cells (CD20). Each histology parameter is given a semi-quantitative score by an Alizee pathologist of: 0=1 not present/normal, 2=minimal, 3=mild, 4=moderate, not disrupting the normal valve architecture, or 4=Marked/Severe with disruption of the normal tissue architecture. These ordinal results are summarized as a mean±SEM for valve radiology and each histology parameter, and a Kruskal-Wallis H test is used compare the two groups. The remaining portions of each valve are placed in individual tissue cassettes, labeled appropriately denoting valve ID, leaflet position and recipient ID, and processed for further analysis.

Immunohistochemical Staining

Additional immune staining is performed to detect expression of matrix metalloproteinases (MMP-1: Ab online rabbit polyclonal [ABIN1869215] and MMP-2: Abcam mouse monoclonal [ab8660]) and osteocalcin (Ab online mouse monoclonal [ABIN190254]). These products have been reported in clinical valves explanted for SVD. Rabbit and mouse primary antibodies are detected using HRP conjugated goat anti-rabbit IgG H&L (Abcam; ab205718) or HRP conjugated goat anti-mouse IgG H&L (ab205719). Immune stains are scored in a blinded manner based on the extent of leaflet with positive staining: 0=negative, 1=1-25%, 2=26-50%, 3=51-75%, and 4=>75%. Glutaraldehyde fixed GalKO and standard pig pericardium is used as a negative control. Positive controls for each specific stain will use formalin fixed samples of normal sheep tissue selected based on the atlas of ovine gene expression. These ordinal immunostaining results are summarized as a Mean±SEM for each stain and a Kruskal-Wallis H test is used compare between the two groups.

Quantitative Analysis of Valve Tissue Calcification

Calcification of the explanted valve tissue is measured quantitatively by inductively coupled plasma mass spectroscopy performed by Legend Technical Services. This analysis is performed in accord with EPA SW 846 method 6020 guidelines for Inductively Coupled Plasma Mass Spectrometry analysis of trace elements. In brief, the remaining portions of each leaflet from each valve are weighed, desiccated at 110° C. for 12 hours, and reweighed to determine the percent solids content. The tissue is digested at 95° C. in a mixture of nitric and hydrochloric acid. The calcium content of the sample, and process blank control, is determined using a Perkin Elmer NexION 330D ICP/MS. The results are reported on a dry weight basis (μg of calcium/mg of tissue). The average calcium content for each valve is calculated and the mean calcification for each valve type is compared using a Student's t-test or Mann-Whitney U-test as appropriate. A p-value of <0.05 is regarded as significant.

Echocardiography Analysis of Valve Performance

Interim and terminal echocardiography is performed to monitor valve pathology and function. These echocardiographic images are analyzed for structural deterioration, hemodynamic performance (regurgitation, mean and peak transvalvular gradients), leaflet motion, cardiac output, thrombosis, and mitral valve dimensions (effective orifice area) of the implanted devices. For each parameter at each time point, a mean±SEM is calculated to compare the two groups across the study duration.

Recipient Immune Response and Systemic Inflammation

Terminal serum samples are collected and analyzed along with interim post-operative samples (SA2) for Gal antibody and anti-Gal specific cytotoxicity as described above. Mean anti-Gal IgM and IgG concentration profiles between GalKO and standard BHV recipients are compared by plotting all individual results and plotting the average for each group to detect valve-dependent induction of Gal antibody. Systemic inflammation in GalKO and standard valve recipients is determined from serial serum samples by C-reactive protein ELISA (Antibodies Online, ABIN832393). Individual and mean results for each group are plotted to detect valve-dependent differences in systemic inflammation.

What is claimed is:

1. A viable genetically modified sheep whose genome comprises a homozygous inactivation of an alpha-1,3-galactosyltransferase (GGTA1) gene, wherein the sheep does not express functional GGTA1 and is capable of producing an antibody that binds galactose alpha 1,3 galactose carbohydrate (Gal) upon administration of Gal, wherein the genetically modified sheep is produced using Cas9 and a guide RNA (gRNA) comprising the nucleic acid sequence of SEQ ID NO: 7.

2. The viable genetically modified sheep of claim 1 produced by fusing an enucleated sheep oocyte with a sheep fibroblast comprising the homozygous inactivation of the GGTA1 gene.

3. A viable genetically modified progeny sheep obtained from the genetically modified sheep of claim 1, wherein the progeny has a genome comprising a homozygous inactivation of a GGTA1 gene, wherein the progeny does not express functional GGTA1 and is capable of producing an antibody that binds Gal.

4. The viable genetically modified progeny sheep of claim 3, wherein the homozygous inactivation of the GGTA1 gene comprises a homozygous mutation or deletion of exon 4 of the GGTA1 gene.

5. The viable genetically modified progeny sheep of claim 3, wherein each allele of the GGTA1 gene comprises the nucleic acid sequence of SEQ ID NO: 2.

6. The viable genetically modified sheep of claim 1, wherein the homozygous inactivation of the GGTA1 gene comprises a homozygous mutation or deletion of exon 4 of the GGTA1 gene.

7. A method of making the viable genetically modified sheep of claim 1, the method comprising:
   a) fusing an enucleated sheep with a sheep fibroblast comprising the homozygous inactivation of the GGTA1 gene such that an embryo whose genome comprises the homozygous inactivation of the GGTA1 gene is obtained;
   b) transferring the embryo to a recipient female sheep;
   c) obtaining the viable genetically modified sheep of claim 1 from the transferred embryo.

8. The viable genetically modified sheep of claim 1, wherein each allele of the GGTA1 gene comprises the nucleic acid sequence of SEQ ID NO: 2.

* * * * *

SEQUENCE LISTING

```
Sequence total quantity: 7
SEQ ID NO: 1              moltype = DNA  length = 522
FEATURE                   Location/Qualifiers
source                    1..522
                          mol_type = other DNA
                          organism = synthetic construct
SEQUENCE: 1
tccagctctt tgcaacgcta tggactgttg cccaccggac acttctgtcc atggaattct   60
ccaggcaaga gtactggagt gggttgccgt gccctccttc aggggggtctt ctccatccag  120
ggatcgaact tgcatctcct gcattgcagg cggattctcc actgctgagc ccctggggaa  180
gcccagaaca tgtgccttag cacttgttaa atattcatca ccttttcctt ttagaaagga  240
cataggtaga aataattatt gaaaaaaatc atatcccact cttgatatat ttaatctatt  300
ttcccccctc ttcttttctt ttcccaggag aaaataatga atgtcaaagg aaaagtgatt  360
ctgtcaatgc tggttgtctc aactgtcatc gttgtgtttt gggaatatat ccacaggtaa  420
ttatggaaca tgataaagtg atgttaatga acgtctccat cagccaagtc accaggttga  480
attgaaatta ggacttcttc cttcctgttt ccctgagccc ta                     522

SEQ ID NO: 2              moltype = DNA  length = 521
FEATURE                   Location/Qualifiers
source                    1..521
                          mol_type = other DNA
                          organism = Synthetic construct
SEQUENCE: 2
tccagctctt tgcaacgcta tggactgttg cccaccggac acttctgtcc atggaattct   60
ccaggcaaga gtactggagt gggttgccgt gccctccttc aggggggtctt ctccatccag  120
ggatcgaact tgcatctcct gcattgcagg cggattctcc actgctgagc ccctggggaa  180
gcccagaaca tgtgccttag cacttgttaa atattcatca ccttttcctt ttagaaagga  240
cataggtaga aataattatt gaaaaaaatc atatcccact cttgatatat ttaatctatt  300
ttcccccctc ttcttttctt ttcccaggag aaaataatga atgtaaagga aaagtgattc  360
tgtcaatgct ggttgtctca actgtcatcg ttgtgttttg ggaatatatc cacaggtaat  420
tatggaacat gataaagtga tgttaatgaa cgtctccatc agccaagtca ccaggttgaa  480
ttgaaattag gacttcttcc ttcctgtttc cctgagccct a                      521

SEQ ID NO: 3              moltype = DNA  length = 20
FEATURE                   Location/Qualifiers
source                    1..20
                          mol_type = other DNA
                          organism = synthetic construct
SEQUENCE: 3
tccagctctt tgcaacgcta                                               20

SEQ ID NO: 4              moltype = DNA  length = 20
FEATURE                   Location/Qualifiers
source                    1..20
                          mol_type = other DNA
                          organism = synthetic construct
SEQUENCE: 4
tagggctcag ggaaacagga                                               20

SEQ ID NO: 5              moltype = DNA  length = 20
FEATURE                   Location/Qualifiers
source                    1..20
                          mol_type = other DNA
                          organism = synthetic construct
SEQUENCE: 5
tccagctctt tgcaacgcta                                               20

SEQ ID NO: 6              moltype = DNA  length = 20
FEATURE                   Location/Qualifiers
source                    1..20
                          mol_type = other DNA
```

```
                        organism = synthetic construct
SEQUENCE: 6
tagggctcag ggaaacagga                                                   20

SEQ ID NO: 7           moltype = DNA  length = 20
FEATURE                Location/Qualifiers
source                 1..20
                       mol_type = other DNA
                       organism = synthetic construct
SEQUENCE: 7
gagaaaataa tgaatgtcaa                                                   20
```